US012784919B2

(12) United States Patent
Hipsley et al.

(10) Patent No.: US 12,784,919 B2
(45) Date of Patent: Nov. 3, 2026

(54) VIRTUAL INTEGRATED REMOTE ASSISTANT APPARATUS AND METHODS

(71) Applicant: Ace Vision Group, Inc., Newark, CA (US)

(72) Inventors: AnnMarie Hipsley, Silver Lake, OH (US); Griffin Peter Thomas, Stow, OH (US)

(73) Assignee: Ace Vision Group, Inc., Newark, CA (US)

( * ) Notice: Subject to any disclaimer, the term of this patent is extended or adjusted under 35 U.S.C. 154(b) by 1077 days.

(21) Appl. No.: 17/894,503

(22) Filed: Aug. 24, 2022

(65) Prior Publication Data

US 2023/0067625 A1 Mar. 2, 2023

Related U.S. Application Data

(60) Provisional application No. 63/237,017, filed on Aug. 25, 2021.

(51) Int. Cl.
*G16H 80/00* (2018.01)
*A61F 9/008* (2006.01)
*G16H 20/00* (2018.01)

(52) U.S. Cl.
CPC ............ *G16H 80/00* (2018.01); *A61F 9/008* (2013.01); *G16H 20/00* (2018.01); (Continued)

(58) Field of Classification Search
CPC ........ G16H 80/00; G16H 20/00; G16H 20/10; G16H 20/40; A61B 3/113; A61F 9/008–2009/00897
See application file for complete search history.

(56) References Cited

U.S. PATENT DOCUMENTS 6,712,808 B2 * 3/2004 Fujieda ............... A61F 9/00821 606/4
8,398,238 B1 * 3/2013 Juhasz .................... A61F 9/008 351/208
(Continued)

FOREIGN PATENT DOCUMENTS

WO WO-2015/021208 A1 2/2015

OTHER PUBLICATIONS

Jakl Andreas et al. (2020). "Enlightening Patients with Augmented Reality," 2020 IEEE Conference on Virtual Reality and 3D User Interfaces (VR), IEEE, Mar. 22, 2020 (Mar. 22, 2020), pp. 195-203, XP033769465. DOI: 10.1109/VR46266.2020.15S1532258804 [retrieved on May 7, 2020].

*Primary Examiner* — Jonathan T Kuo
(74) *Attorney, Agent, or Firm* — Mintz Levin Cohn Ferris Glovsky and Popeo, P.C.

(57) ABSTRACT

A system for a virtual integrated remote assistant is provided. In some implementations, the system performs operations comprising receiving an input for a surgical procedure. The operations further include determining first feedback for the surgical procedure. The operations further include receiving, in response to the first feedback, a user input. The operations further include receiving second feedback from a laser apparatus. The operations further include performing eye tracking verification for a user. The operations further include displaying a graphical display of a virtual assistant. Related systems, methods, and articles of manufacture are also described.

18 Claims, 48 Drawing Sheets

(52) U.S. Cl.
CPC ............... *A61F 2009/00846* (2013.01); *A61F 2009/00887* (2013.01); *A61F 2009/00893* (2013.01)

(56) References Cited

U.S. PATENT DOCUMENTS

| | | | | |
|---|---|---|---|---|
| 2002/0040218 | A1* | 4/2002 | Fujieda | A61F 9/00821 351/200 |
| 2013/0050649 | A1* | 2/2013 | Juhasz | A61F 9/008 351/208 |
| 2016/0095752 | A1 | 4/2016 | Srinivasan et al. | |
| 2019/0313893 | A1 | 10/2019 | Eil | |
| 2020/0258609 | A1* | 8/2020 | McMaster | G16H 10/40 |
| 2022/0183546 | A1* | 6/2022 | Padula | A61B 3/0041 |
| 2022/0354440 | A1* | 11/2022 | Grajales | A61B 5/7465 |
| 2023/0142530 | A1 | 5/2023 | Hipsley et al. | |
| 2023/0181365 | A1* | 6/2023 | Vogelsang | A61F 9/00804 606/3 |
| 2023/0351073 | A1 | 11/2023 | Hipsley et al. | |

* cited by examiner

VIRA Integrated GUI Control

- Could potentially use Icon Menu Bar to GOTO MPT or any sub-screen, OCT sub screen etc.
- Could also use the tabs
- VIRA is interactive now with the surgeon she can speak or ask or suggest to the doctor what screens to go to.
- VIRA also can be spoken to VOIP if the surgeon is remote.
- This is useful LIVE since VIRA can run the screens for the surgeon without need of a technician.

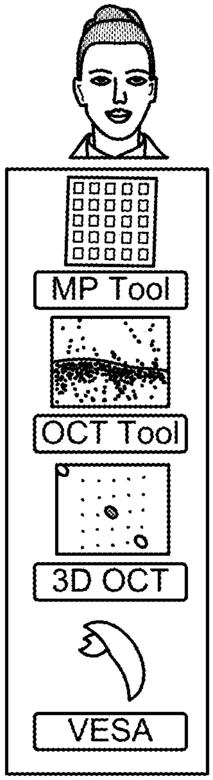

FIG. 2

VIRA: Virtual Clinical Experience

Log-in

Log-in

VIRA x

Dioptor information

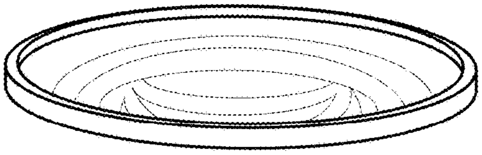

What is a diopter ?

A Close-Up Lens is NOT a Diopter!OK, it's time for me to rant a bit about "Diopters"Close-Up lenses or close-up filters are accessories mounted in front of photographic lenses and cine lenses to enable focusing closer than the lens will do by itself....

"Proceed to this website to learn more about your diopter value - yes/not right now".

https://www.lindseyoptics.com/blog/what-is-a-diopter/

CONTINUE

Patient Flow / Login – Sign Up

- Diopter(Sign Up)

Comments:

1. Login Screen: You can login to the application if you are already registered

2. Sign Up Screen: Need to fill in details to access the application by logging in.

3. Diopter information: On selecting the diopter value information you can see this a popup screen.

FIG. 11B

Patient Data/Evaluation

Patient Data/Evaluation

Patient Data/Evaluation

How much diffculty do you have

1. Reading small print, such as : newspaper articles, items on a menu, telephone directories?

- ○ N/A or stopped for non-visual reasons
- ○ No Difficulty
- ○ A Little Difficulty
- ○ Moderate Difficulty
- ○ Extreme Difficulty 2. Reading lables/ instructions/ ingredients/ prices such as on medicine bottles, food packaging?

- ○ N/A or stopped for non-visual reasons
- ○ No Difficulty
- ○ A Little Difficulty
- ○ Moderate Difficulty
- ○ Extreme Difficulty 3. Reading your post/ mail, such as: electric bill, greeting cards, bank statements, letters from friends & family?

FIG. 15

Patient Data/Evaluation

Patient Data/Evaluation

Patient Flow / Home V.2 - Exercise Tab

Comments:

In the new home screen when we click the Test your eye Tab.

The next screen would appear which says the Featured exercise

Below given a tab which gives you an option of Book your next appointment.

The next option gives you to select the Category Tab which has options like Lasik, Presbyopia, Cataract & Surgery .

On clicking on the featured exercise, you would go to next screen

FIG. 19D

Patient Flow – Home Screen
Option 3-Not using

Patient Flow / Surgery Status – Final Report

Comments: yet to be decided as what needs to come in over here.

Scheduling Agent

VIRTUAL INTEGRATED REMOTE ASSISTANT APPARATUS AND METHODS

CROSS REFERENCE TO RELATED APPLICATIONS

This application claims priority to U.S. Patent Application No. 63/237,017 filed Aug. 25, 2021, entitled "VIRTUAL INTEGRATED REMOTE ASSISTANT APPARATUS AND METHODS", the contents of which is hereby incorporated by reference herein in its entirety.

TECHNICAL FIELD

The subject matter described herein relates to remote eye surgery training, eye exercises, visual therapy, visual rehabilitation, visual eye exams, find my doctor appointment scheduling, and more particularly, a virtual integrated remote assistant (VIRA).

BACKGROUND

Laser eye therapies (e.g., surgery) and ophthalmic therapeutics administered in various locations on the eye can require high levels of accuracy and precision to restore natural visual accommodation for better near, intermediate, and distance vision for the more than 1 billion presbyopes who do not currently have a therapeutic solution to treat their condition. Many hours to years of education and training are essential for successful operations, treatments, therapeutics, and the like.

Current ophthalmic surgical experiences rely physical interactions between a patient and medical professionals (e.g., technicians, surgeons, assistants, etc.). It may be beneficial to provide certain information to the patient regarding the current, specific surgical procedure and what to expect before, during, and after the procedure. A virtual assistant may be configured to simulate a person, in some respects, so that the patient undergoing a surgical procedure may be educated on the procedure and what to expect on the procedure day.

It is therefore desirable to provide improved systems, devices and methods for performing ocular procedures.

SUMMARY

In some aspects, a method, computer program product and system are provided. In an implementation, a virtual integrated remote assistant system is provided.

Disclosed are remote procedures which are performed in various states, e.g., "autonomous", "semiautonomous," and/or "telerobotic." Disclosed are an autonomous chatbot widget that connects patients to doctors as well as manages simple and complex tasks.

Disclosed are an integrated evaluation upon sign up in which measures a patient's diopter value of both eyes based on distance measurements derived from phone sensor analysis of patient focus capabilities to then be calculated into a value of human eye diopters.

Disclosed are virtually integrated remote assistants that are controlled in part by a neural network or deep learning artificial intelligence processor and a software agent.

In some variations, the virtual integrated remote assistant may be implemented on a software application or on a user interface of a laser apparatus.

Implementations of the current subject matter can include systems and methods consistent with the present description, including one or more features as described, as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

In one aspect, there is disclosed a method comprising: receiving, by a processor, an input for a surgical procedure wherein the surgical procedure relates to an eye or an ophthalmic procedure; determining, by the processor, first feedback for the surgical procedure; receiving, by the processor and in response to the first feedback, a user input; receiving, by the processor, second feedback from a laser apparatus; performing, by the processor, eye tracking verification for a user; and displaying, by the processor, a graphical display of a virtual assistant.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

The systems, devices, and methods described herein in detail for laser ocular microporation are example embodiments and should not be considered limiting. Other configurations, methods, features and advantages of the subject matter described herein will be or will become apparent to one with skill in the art upon examination of the following FIGURES and detailed description. It is intended that all such additional configurations, methods, features and advantages be included within this description, be within the scope of the subject matter described herein and be protected by the accompanying claims. In no way should the features of the example embodiments be construed as limiting the appended claims, absent express recitation of those features in the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 2 depicts an example graphical user interface control, in accordance with some example implementations;

FIGS. 9, 10, 11A, and 11B depict example virtual assistant application log-in user interfaces, in accordance with some example implementations;

FIGS. 15, 16A, and 16B depict example virtual assistant application patient evaluation user interfaces, in accordance with some example implementations;

FIGS. 19A, 19B, 19C, 19D, 19E, and 19F depicts an example virtual assistant application home screen and navigation user interfaces, in accordance with some example implementations;

When practical, similar reference numbers denote similar structures, features, or elements.

DETAILED DESCRIPTION

Figure 1:
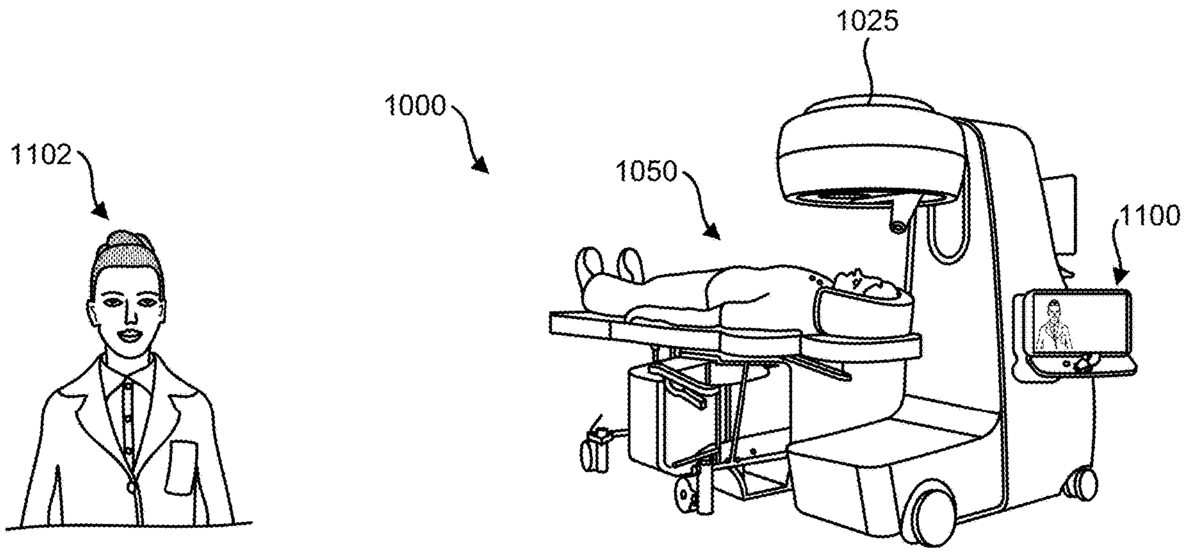
FIG. 1 depicts a system for eye surgery, in accordance with some example implementations.

As noted above and as detailed below, embodiments of methods and devices described herein include a number of aspects which may be usefully employed in combination or separately, and which may be advantageously used to treat a range of disease conditions, both of the eye and other regions of the body. At least some of the examples described in particular detail focus on treatment of conditions of the eye, such as the treatment of age-related glaucoma, cataract formation, and other age-related ocular diseases such as age-related macular degeneration, or the like.

In particular, embodiments described herein relate to a hardware and software system solution used for a virtual integrated remote assistant system. The virtual integrated remote assistant system may provide human-like assistance to the patient and/or surgeon for a medical procedure. Such assistance may improve surgery by at least providing education and feedback before, during, and/or after surgery than other surgical assistance.

The systems, devices and methods of the present disclosure include but are not limited to a surgical laser procedure such as ophthalmic procedures (e.g., a cataract surgery, a cataract LASIK surgery, a FemtoSecond surgery, an MIGS implant surgery, a Keratoconus surgery, or the like), presbyopic procedures such as Laser Scleral Microroporation (LSM) and orthopedic procedures (e.g., laser disc surgery).

In some aspects, ophthalmic surgical or therapeutic or diagnostic procedures may rely on physical interactions between a patient and medical professionals (e.g., technicians, surgeons, assistants, etc.). In some implementations, it may be beneficial to reduce or eliminate a number of persons in an operating room for the surgical procedure. For example, during a pandemic (e.g., COVID-19 or the like) it may be necessary to reduce or eliminate physical interactions between a patient and one or more medical professionals by creating access for a remote or telerobotic surgery. Embodiments described herein directed to a virtual integrated remote assistant may reduce or eliminate physical interactions between the patient and medical professionals while still retaining a high standard of care for the patient.

For example, the virtual integrated remote assistant (VIRA) may educate the patient on the procedure and what to expect on the procedure day. In some aspects, framing of procedure information may protect providers and patients. VIRA may facilitate integrated telehealth and may create an ultra-minimally invasive environment between the doctor and the patient. VIRA may be a software agent that is human-like visually, verbally, and physical gestures and movements.

In some aspects, on the procedure day, VIRA may inform the patient or medical professional on what will happen during the procedure and provide instructions to the patient or medical professional to facilitate a successful surgical procedure. For example, VIRA may instruct the patient to practice looking at fixation points to expose four quadrants of the sclera and may inform the patient of a post-operative regimen. In some aspects, VIRA may remind the patient to take their prescribed medication and schedule for postoperative visits via email, text, mobile application, or other communication. In some aspects, VIRA may refer patients to specified treatments, medical professionals, or facilities based off of obtained patient data.

FIG. 1 depicts a system 1000 for eye surgery, in accordance with some example implementations. As shown, the system 1000 includes a laser apparatus 1025, a patient 1050, a user interface 1100, and a virtual integrated remote assistant 1102. In some aspects, the user interface 1100 may be integrated in at least a portion of the laser apparatus 1025.

FIG. 2 depicts an example graphical user interface (GUI) control, in accordance with some example implementations. The GUI control may use an icon menu bar to provide navigation to different screens (e.g., an optical coherence tomography (OCT) screen, a three dimensional screen, a holographic screen, or the like. The GUI control may also use tabs for navigation. In some aspects, VIRA may interact with the doctor or surgeon and provide information, visuals, or other feedback to aid in the surgical procedure. The feedback may include instructing the patient to practice looking at fixation points to expose four quadrants of the sclera and may inform the patient of a post-operative regimen. VIRA may be spoken to using voice over IP (VOIP) or other voice communication if the surgeon is remote. This voice controlled aspect may be beneficial in real time since VIRA can run screens (e.g., cameras or images of the surgery area) for the surgeon without the need of a technician.

Figure 3:
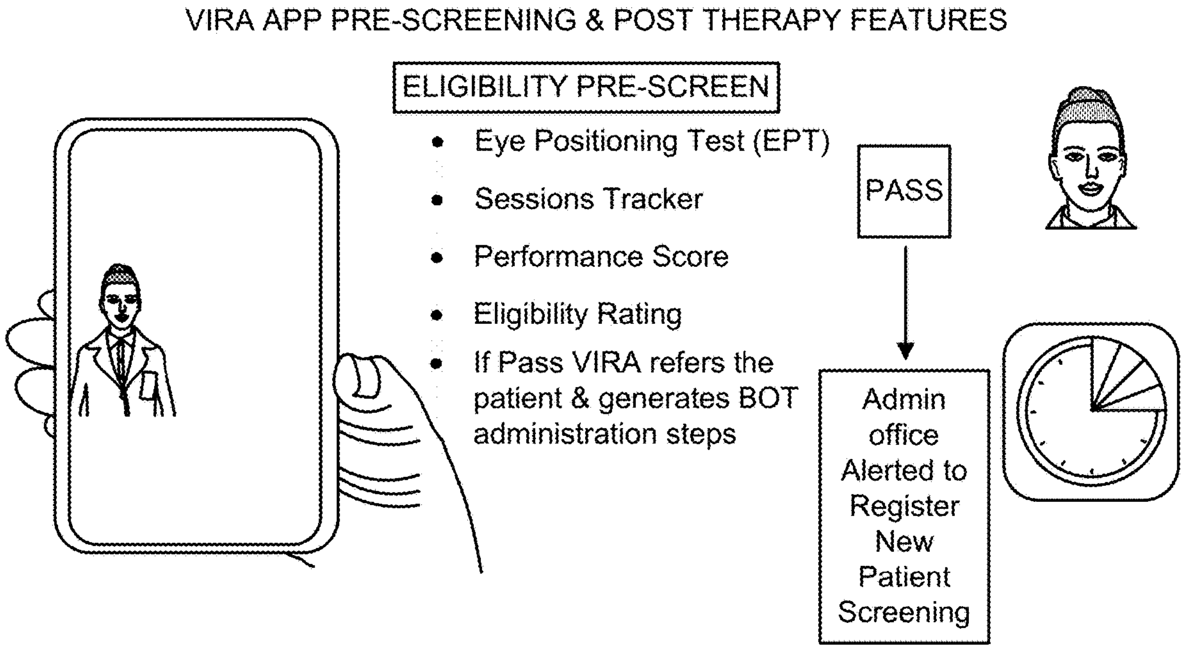
FIG. 3 depicts an example virtual assistant application pre-screening and post therapy features, in accordance with some example implementations.

FIG. 3 depicts an example virtual assistant application pre-screening and post therapy features, in accordance with some example implementations. In some implementations, the pre-screening may include visual tests to determine a medical condition or vision status. In some aspects, VIRA may be implemented on a software app of a smart phone, tablet, laptop, smart watch, or other computing and/or wearable device. FIG. 3 shows VIRA application providing an eye positioning test (EPT) and a screen showing the user past the EPT. The user may then alert an administration office to register the user as a new patient and include the results of the EPT as part of the patient screening process.

Figure 4:
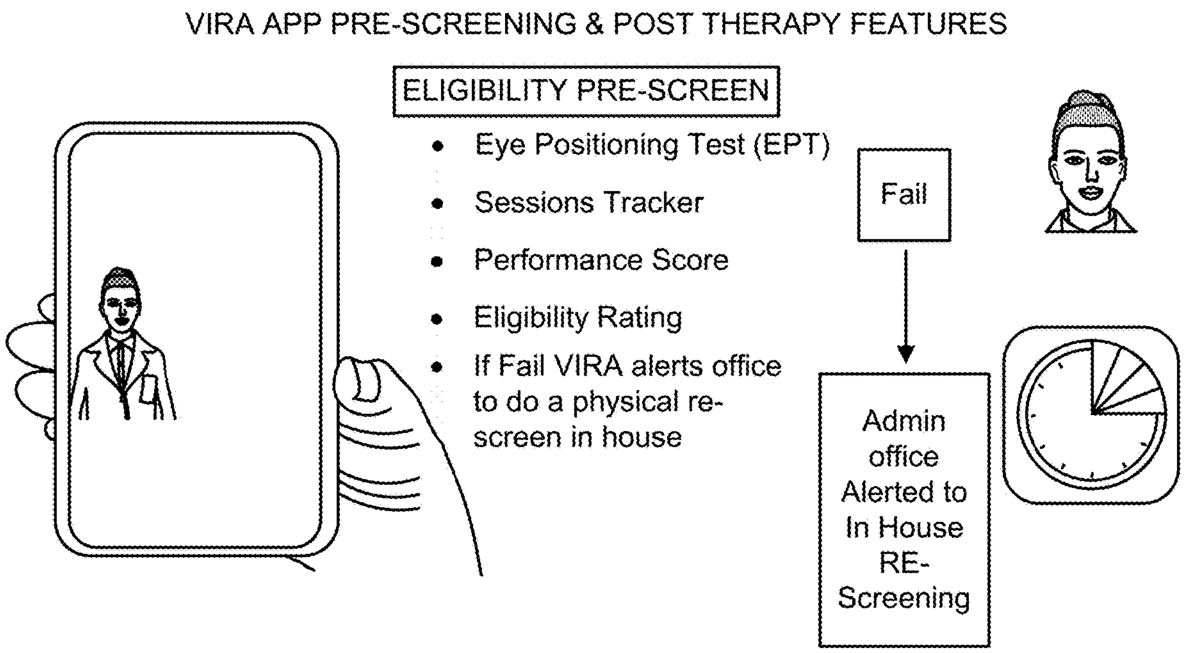
FIG. 4 depicts an example virtual assistant application pre-screening and post therapy features, in accordance with some example implementations.

FIG. 4 depicts an example virtual assistant application pre-screening and post therapy features, in accordance with some example implementations. In the example of FIG. 4, the user has failed the EPT and an administration office may be alerted as to the results of the EPT.

Figure 5:
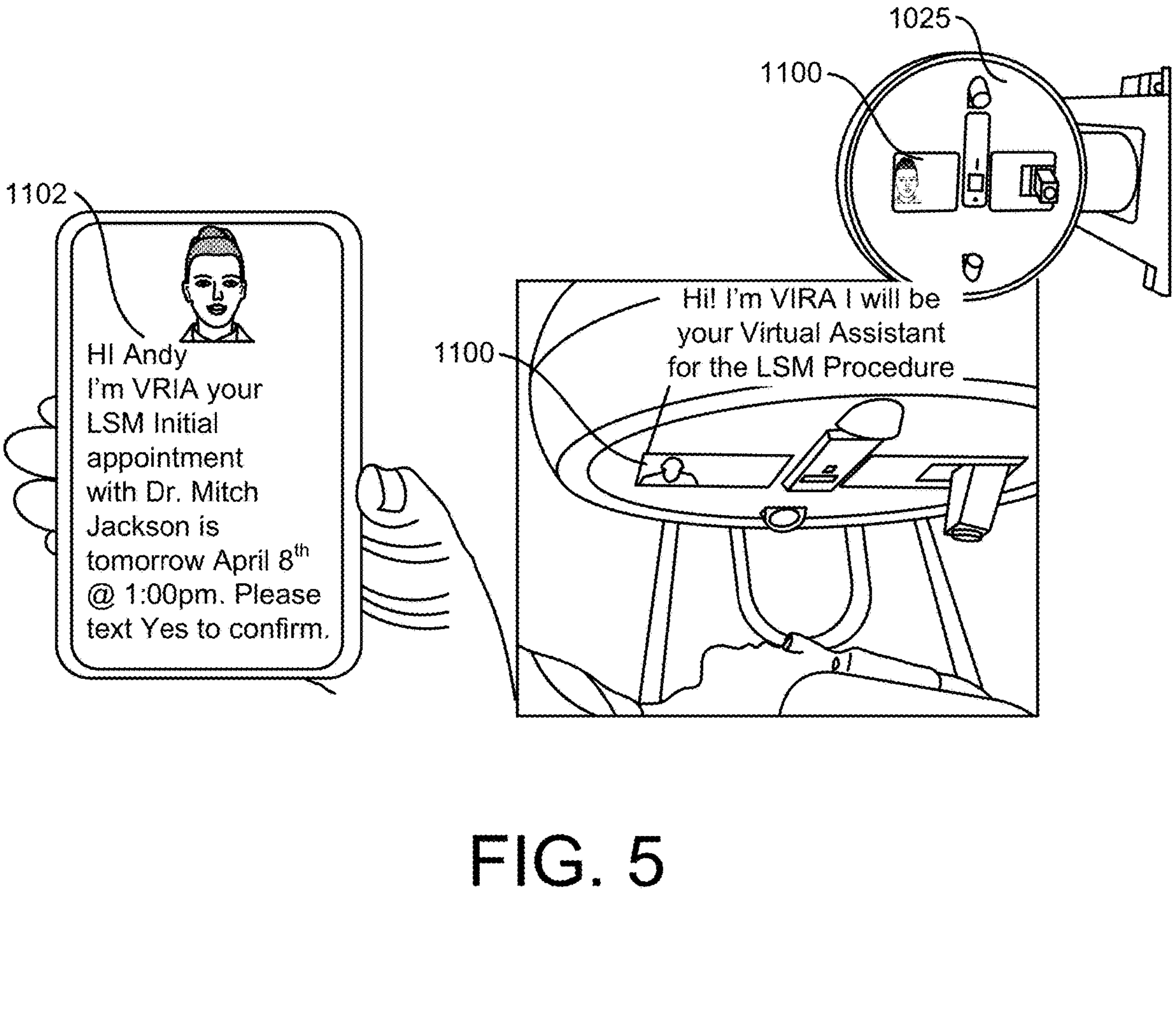
FIG. 5 depict an example virtual assistant user interface, in accordance with some example implementations.

FIG. 5 depict an example virtual assistant user interface 1100 disposed on a surface of the laser apparatus 1025, in accordance with some example implementations. As further shown, the virtual integrated remote assistant 1102 is integrated in a mobile application on a smart phone. In some aspects, the position of the user interface 1100 may allow a patient to view the virtual integrated remote assistant 1102 during a surgical procedure and receive instructions from the virtual integrated remote assistant 1102 during the procedure.

Figure 6:
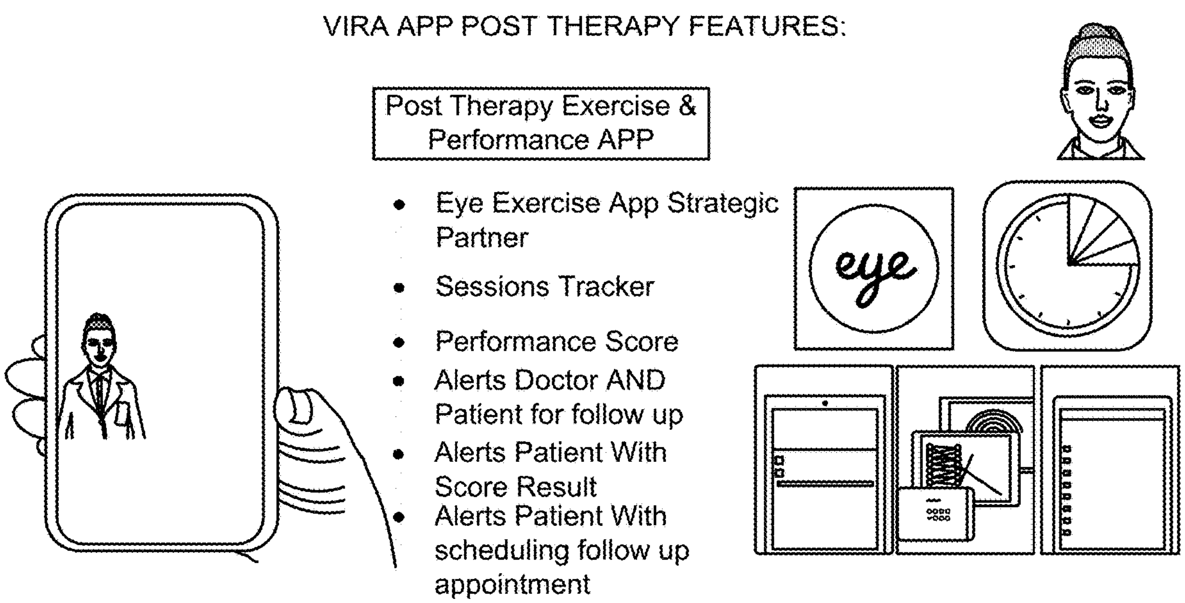
FIG. 6 depicts example virtual assistant application post therapy features, in accordance with some example implementations.

FIG. 6 depicts an example virtual assistant application post procedure/therapy features, in accordance with some example implementations. As shown, the virtual assistant application may provide vision exercises, exercise sessions tracking, performance scores, or the like to aid in post surgical recovery for the patient. The virtual assistant may also make recommendations from the web or other portal. The virtual assistant application may also alert the doctor and/or the patient regarding follow-up appointments and/or treatments. The virtual assistant application may also be configured to alert the patient and/or the doctor with performance score results and may alert the patient with scheduling follow-up appointments.

Figure 7:
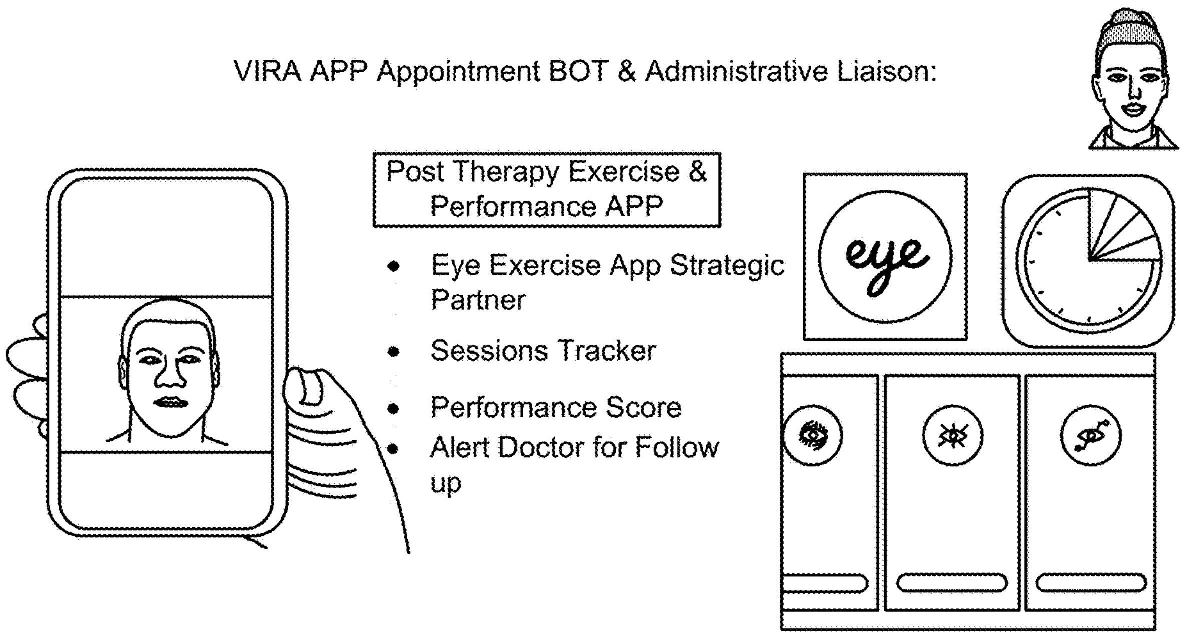
FIG. 7 depicts an example virtual assistant application appointment and administration features, in accordance with some example implementations.

FIG. 7 depicts an example virtual assistant application appointment and administration features, in accordance with some example implementations. As shown, the virtual assistant application may provide an eye exercise application strategic partner, exercise sessions tracking, a performance score based on the exercise sessions, and may provide an alert to a doctor for follow-up. Virtual Assistant may provide alarms, alerts and calendar reminders to patients, doctors, technicians or any approved member added to a thread or user group.

Figure 8:
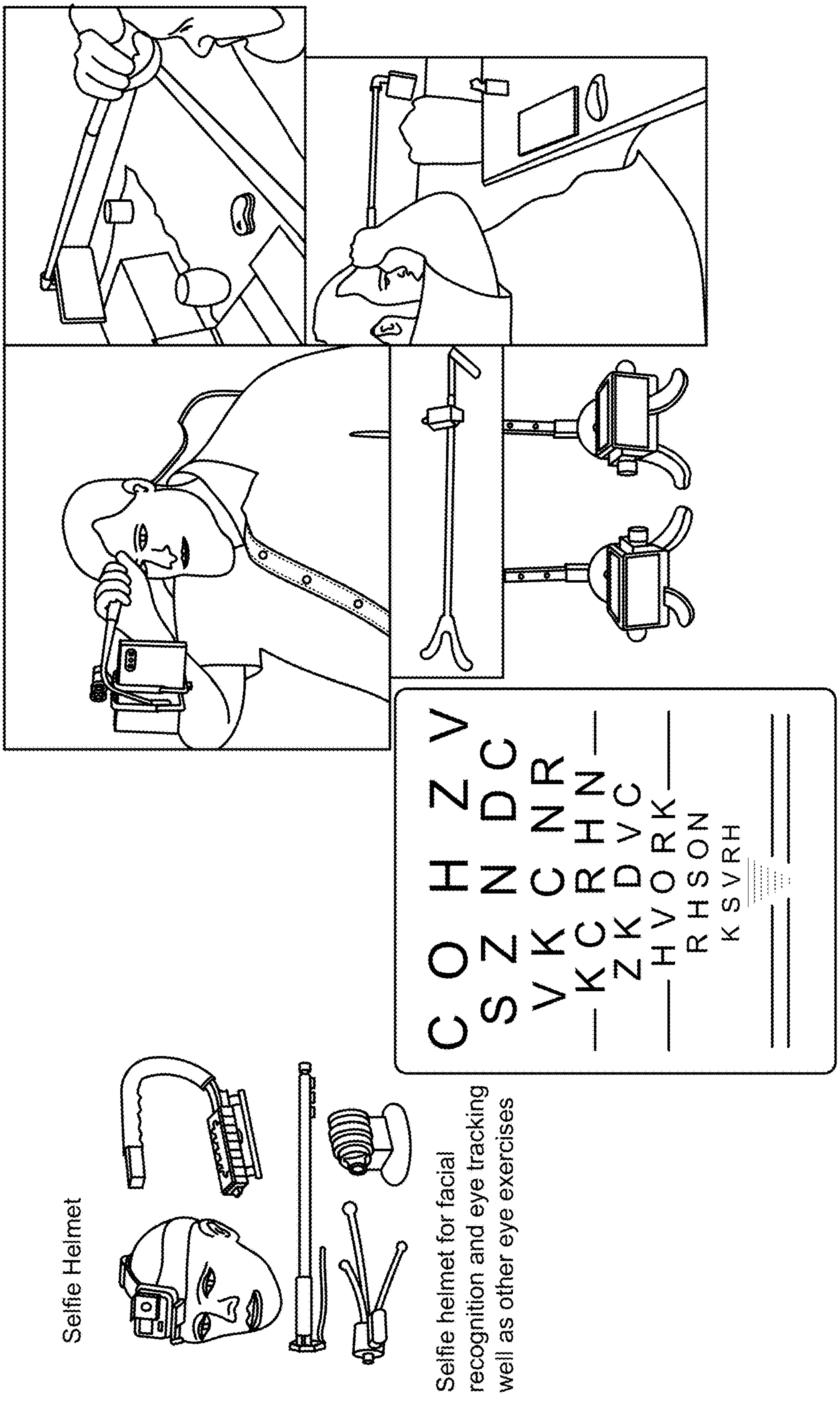
FIG. 8 depicts an example selfie helmet assembly, in accordance with some example implementations.
Figure 9:
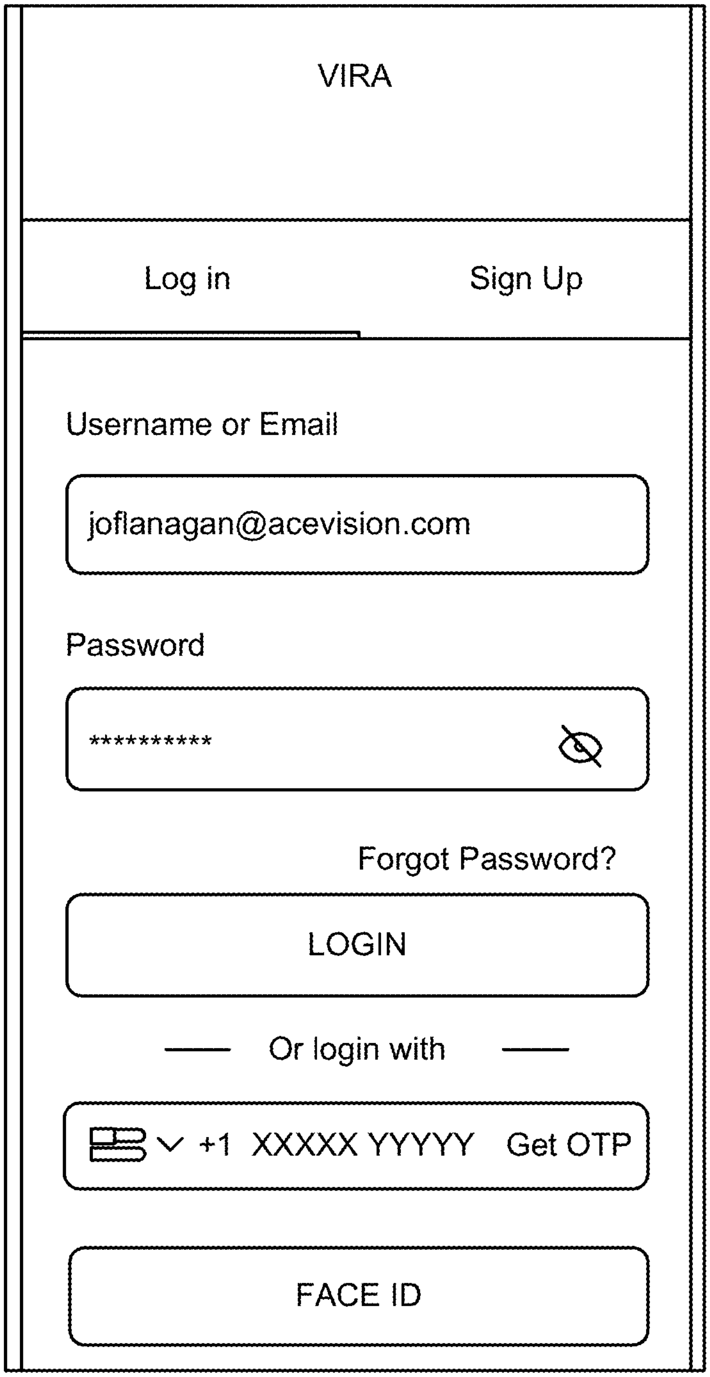
Figure 10:
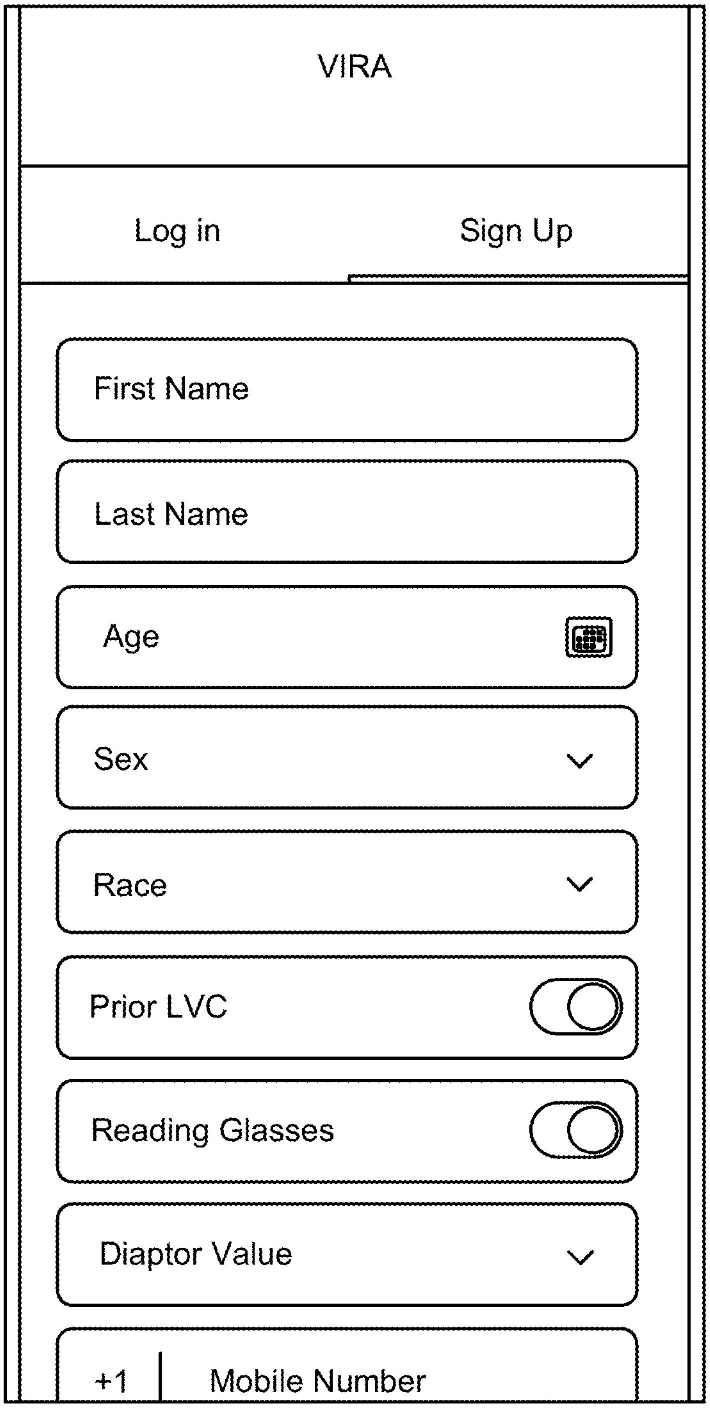

FIG. 8 depicts an example selfie helmet assembly, in accordance with some example implementations. In some aspects, the selfie helmet assembly may facilitate positioning the virtual integrated remote assistant 1102 on a user interface in the field of view of the patient. The selfie helmet assembly may also facilitate facial recognition and eye tracking as well as other eye exercises for the patient.

FIGS. 9, 10, 11A and 11B depict example virtual assistant application log-in user interfaces, in accordance with some example implementations. In some aspects, the virtual assistant application may provide a login for the patient and create a profile for that patient.

Figure 11A:
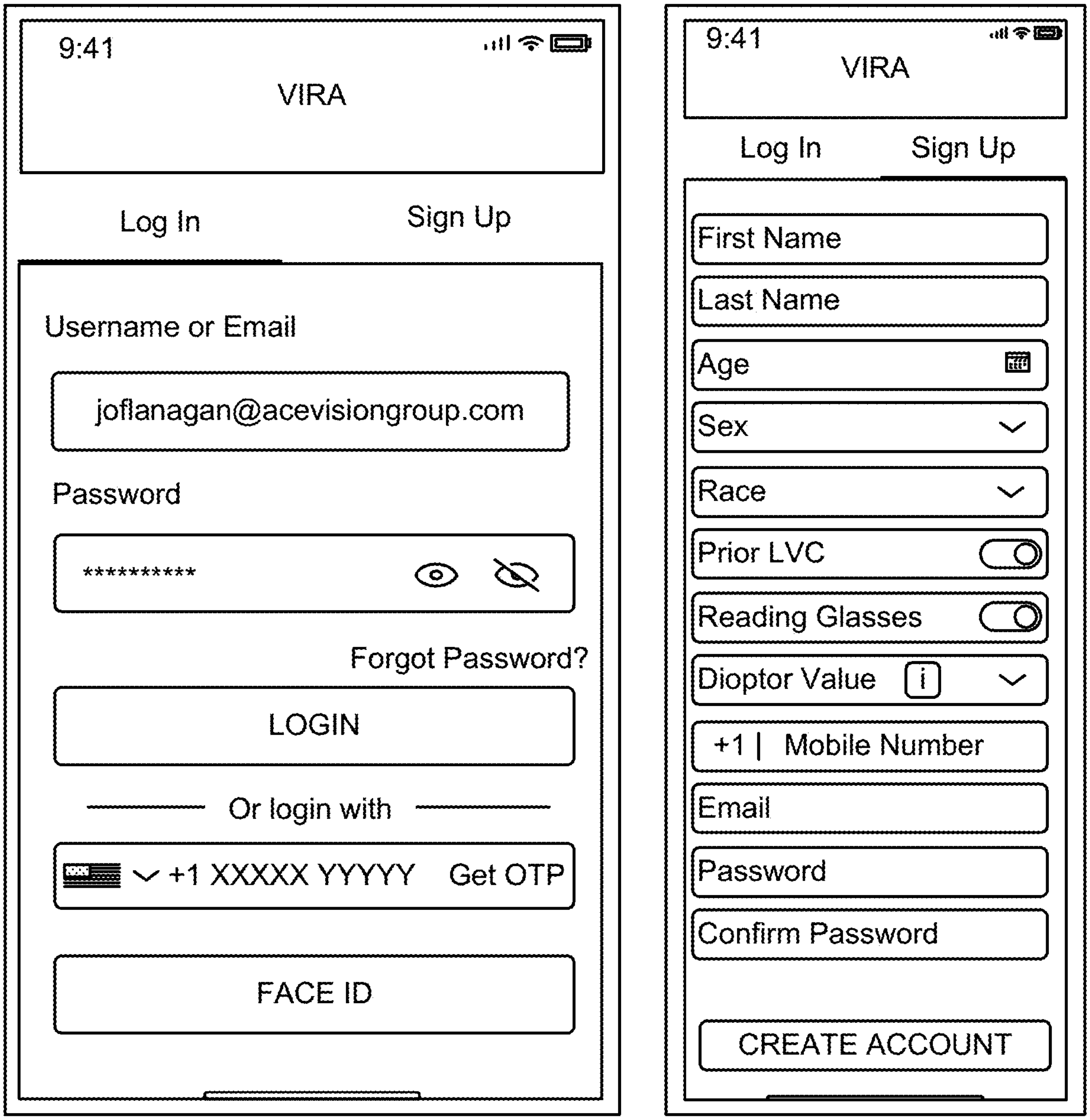
Figure 11C:
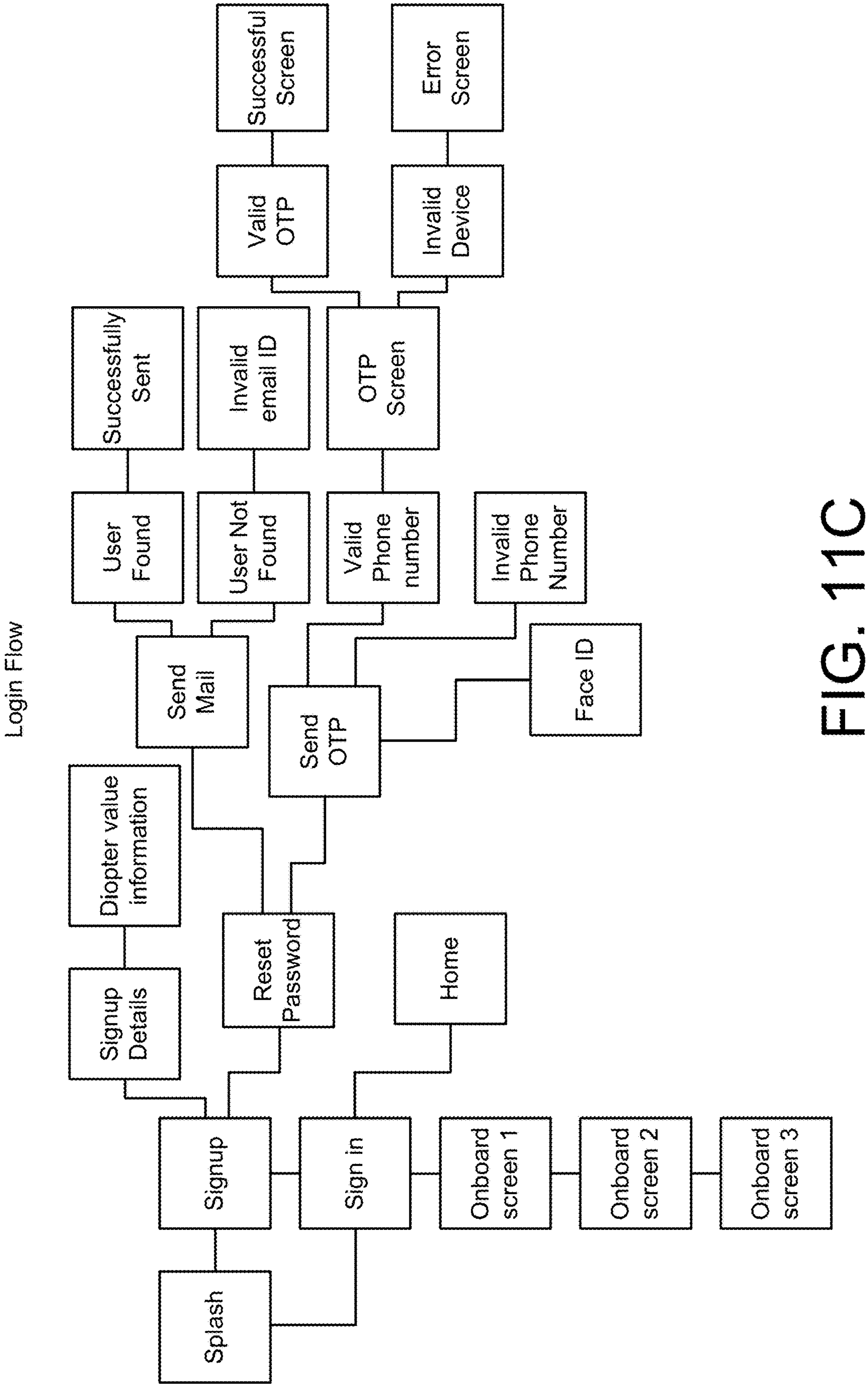
FIG. 11C depicts an example of the flow in which the login process will commence.

FIG. 11C depicts an example of the flow in which the login process will commence. Upon signing up after the splash screen, the application will commence in prompting the user with screens in correspondence to what is shown.

Figure 12:
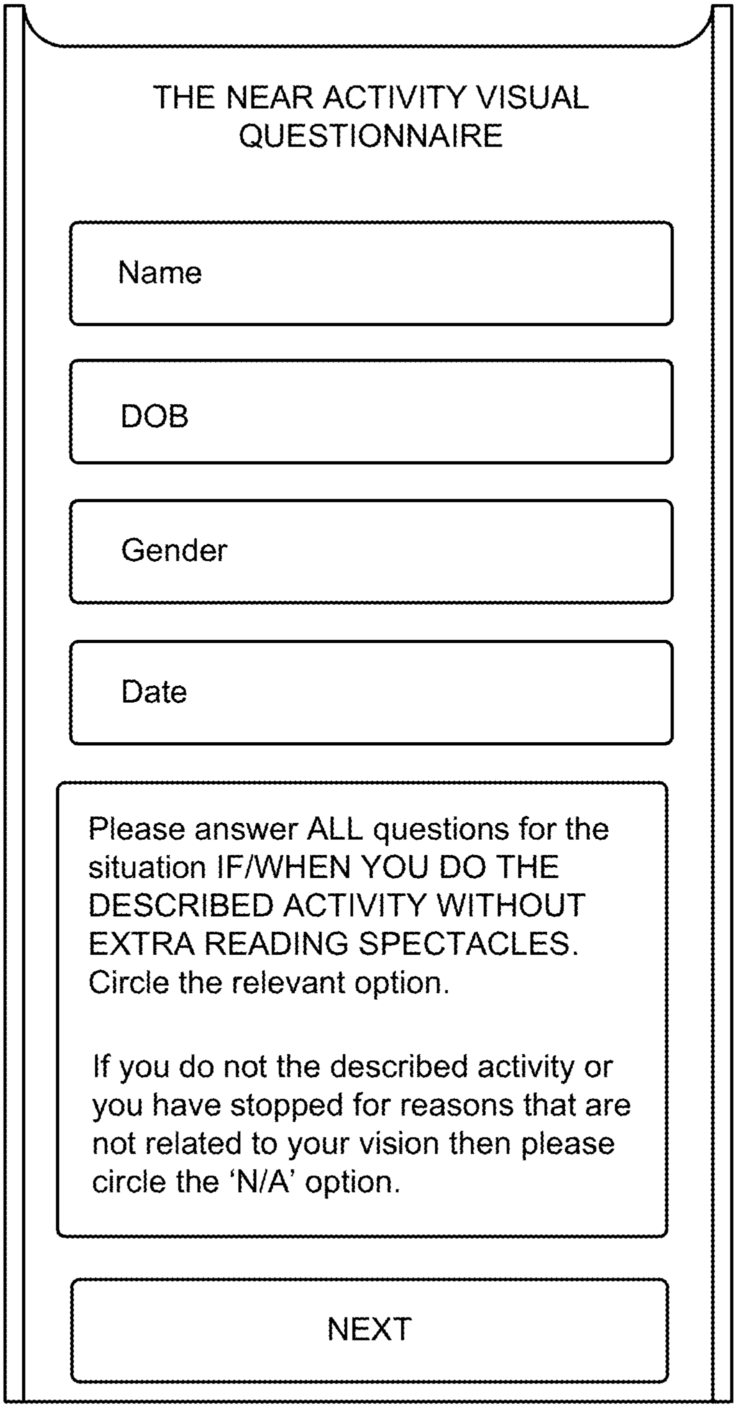
FIG. 12 depicts an example virtual assistant application patient data and/or evaluation features, in accordance with some example implementations.

FIG. 12 depicts an example virtual assistant application patient data and/or evaluation features, in accordance with some example implementations. In some aspects, a patient profile may include answers to a visual questionnaire as shown in the example of FIG. 12.

Figure 13:
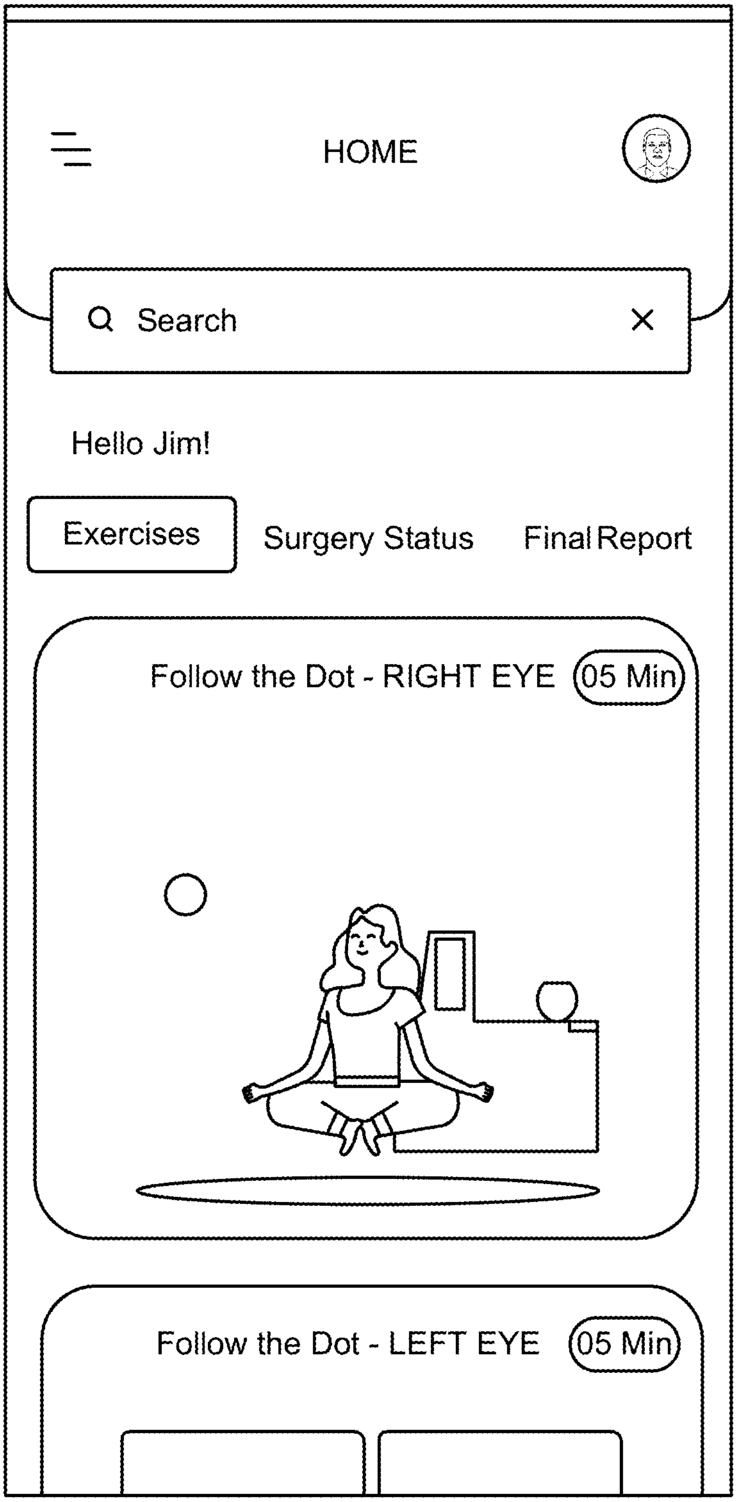
FIGS. 13 and 14 depict example virtual assistant application patient data and/or evaluation user interfaces, in accordance with some example implementations.
Figure 14:
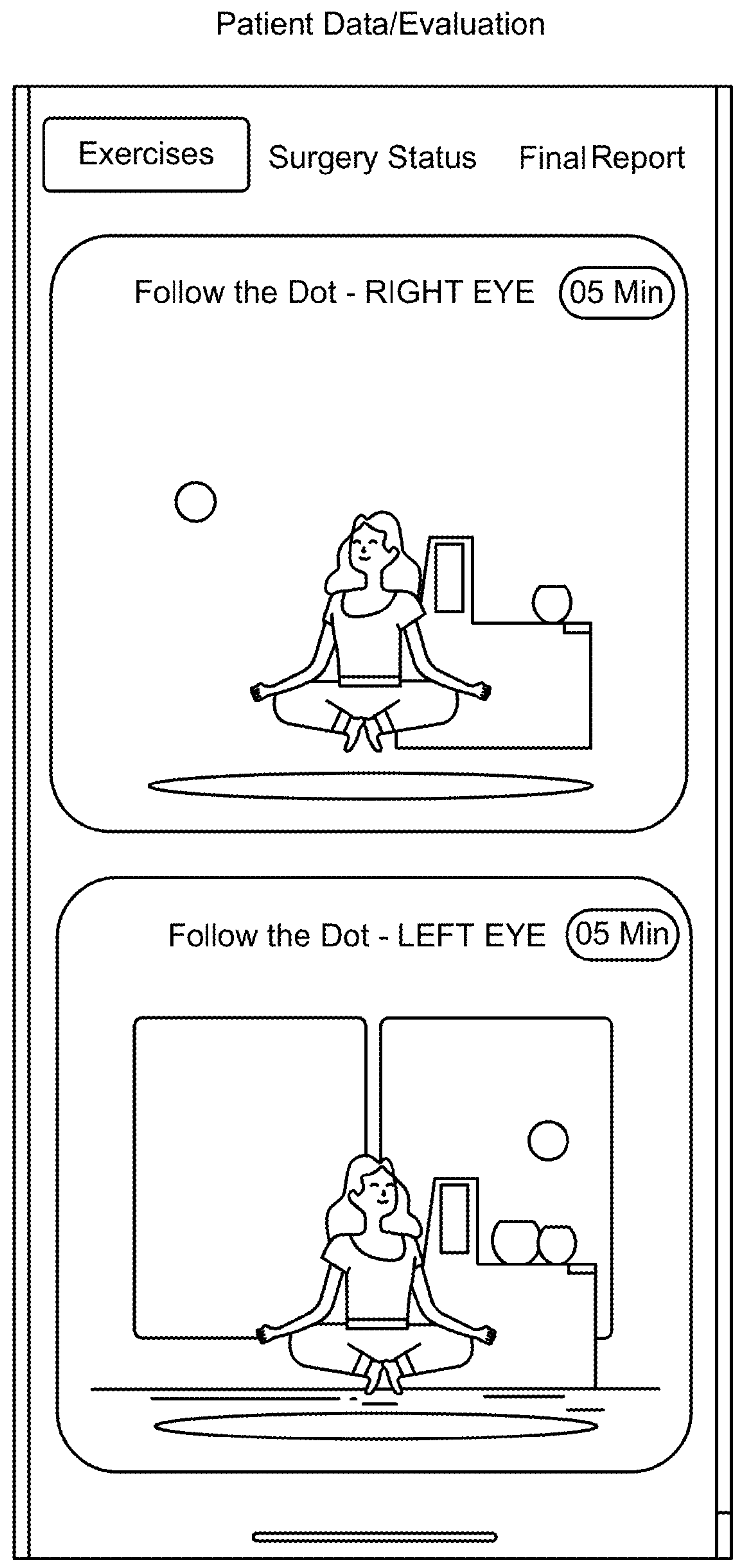

FIGS. 13 and 14 depict example virtual assistant application patient data and/or evaluation user interfaces, in accordance with some example implementations. In some aspects, the virtual assistant application may provide exercises, information, surgery status, and medical evaluations to the patient. As shown, the virtual assistant application may provide exercises for each eye of the patient and may record the results locally or on a server.

Figure 16A:
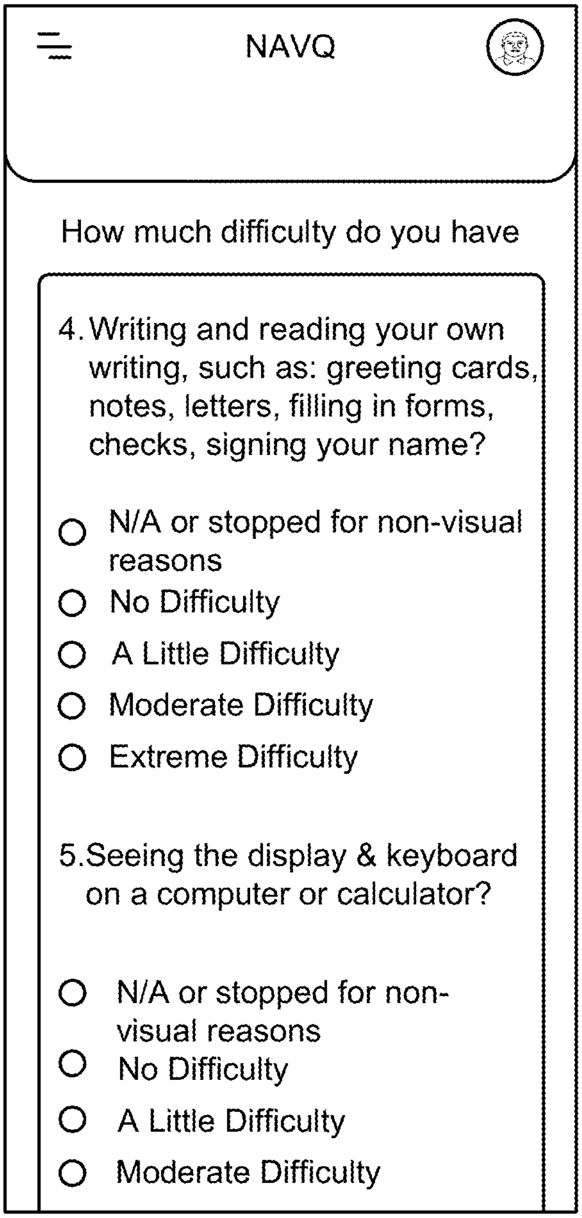
Figure 16B:
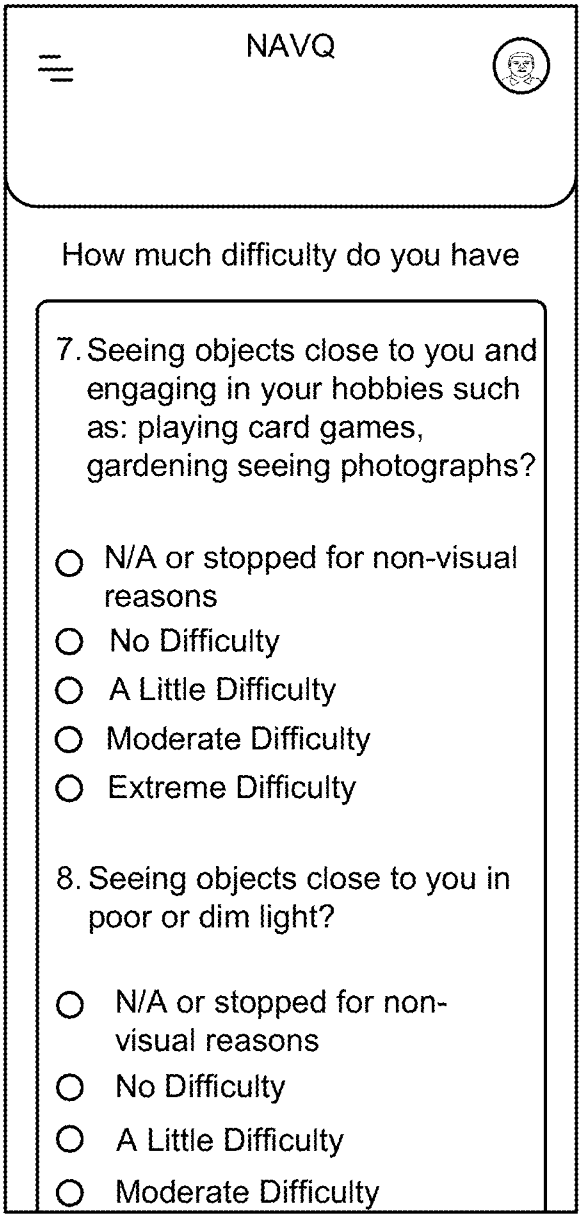

FIGS. 15 and 16A, and 16B depict example virtual assistant application patient evaluation user interfaces, in accordance with some example implementations. In some aspects, a patient profile may include answers to a visual questionnaire as shown in the examples of FIGS. 15-16B.

Figure 17A:
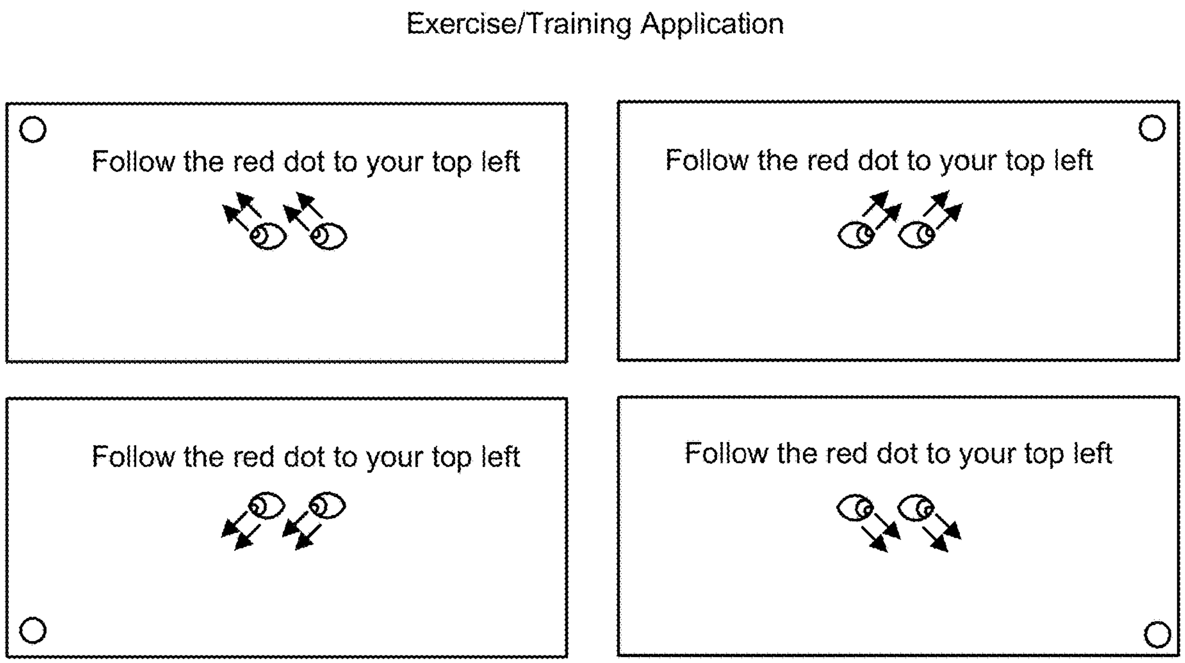
FIG. 17A depicts an example virtual assistant application and exercise/training user interfaces, in accordance with some example implementations.

FIG. 17A depicts a set of example virtual assistant application exercises/training user interfaces, in accordance with some example implementations. As shown, the virtual assistant application may instruct the user to follow a fixation target (e.g., a red dot) on the screen.

Figure 17B:
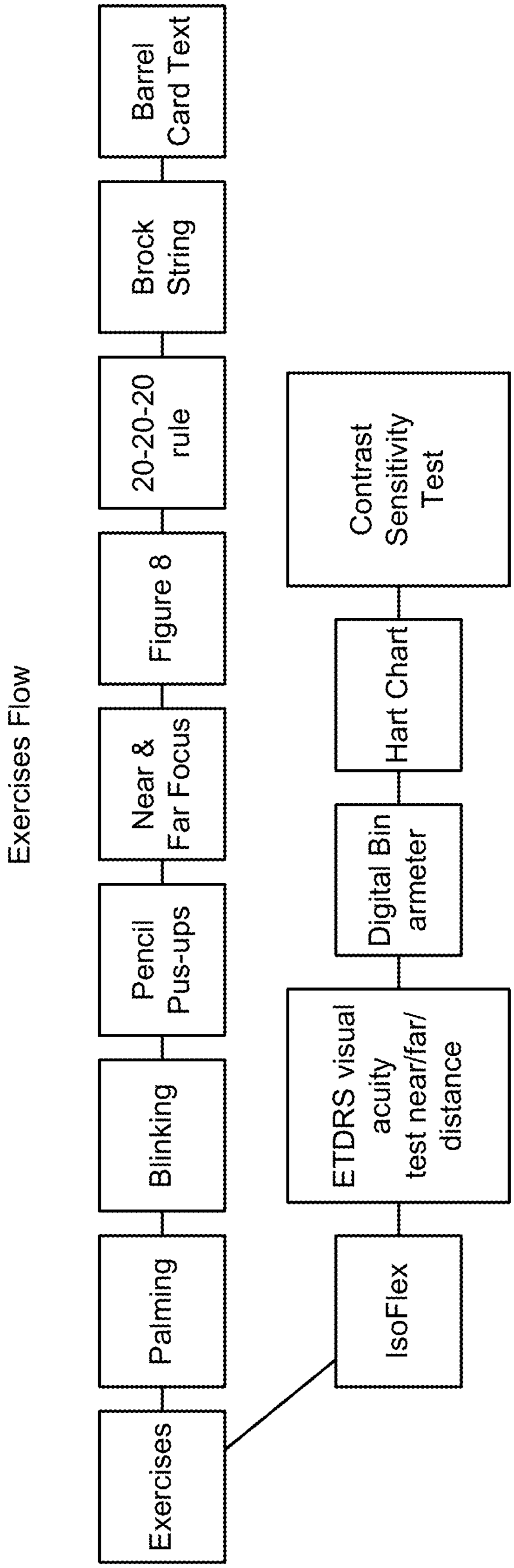
FIG. 17B depicts an example of the flow in which the application may run a patient through each exercise.

FIG. 17B depicts an example of the flow in which the application may run a patient through each exercise. As shown, exercises consist of but is not limited to, palming, blinking, pencil push-ups, near & far focus, rule, brock string, barrel card text, IsoFlex, ETDRS visual acuity cards, digital binarmeter, hart chart, and contrast sensitivity test.

Figure 17C:
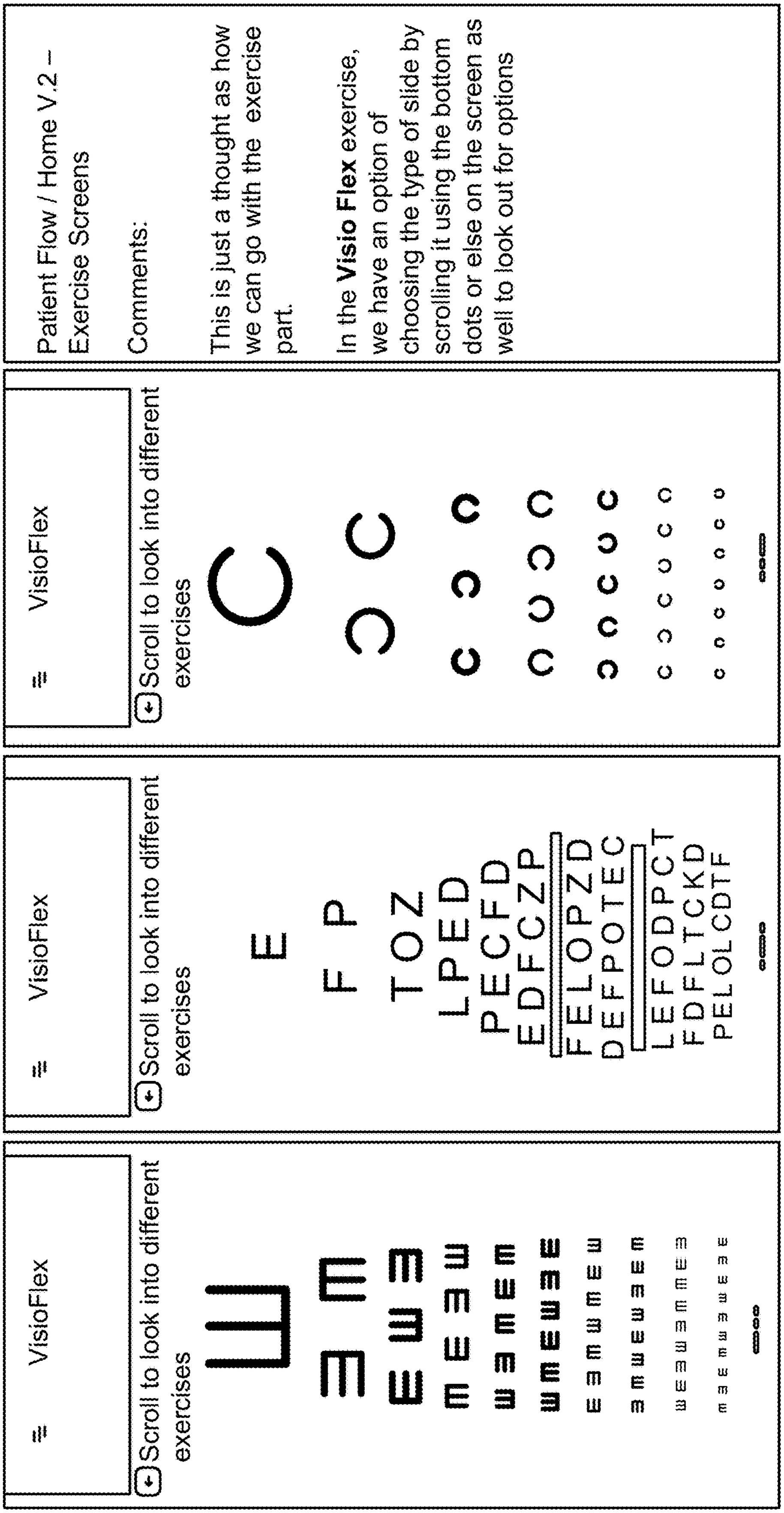
FIG. 17C depicts an example of the method in which a patient would read a VisioFlex digital chart of symbols and characters testing the patient's visual acuity.

FIG. 17C depicts an example of the method in which a patient would read a VisioFlex digital chart of symbols and characters testing the patient's visual acuity. This is done by analyzing the patient's reading capability via holding the cellular device various distances away from their field of vision.

Figure 17D:
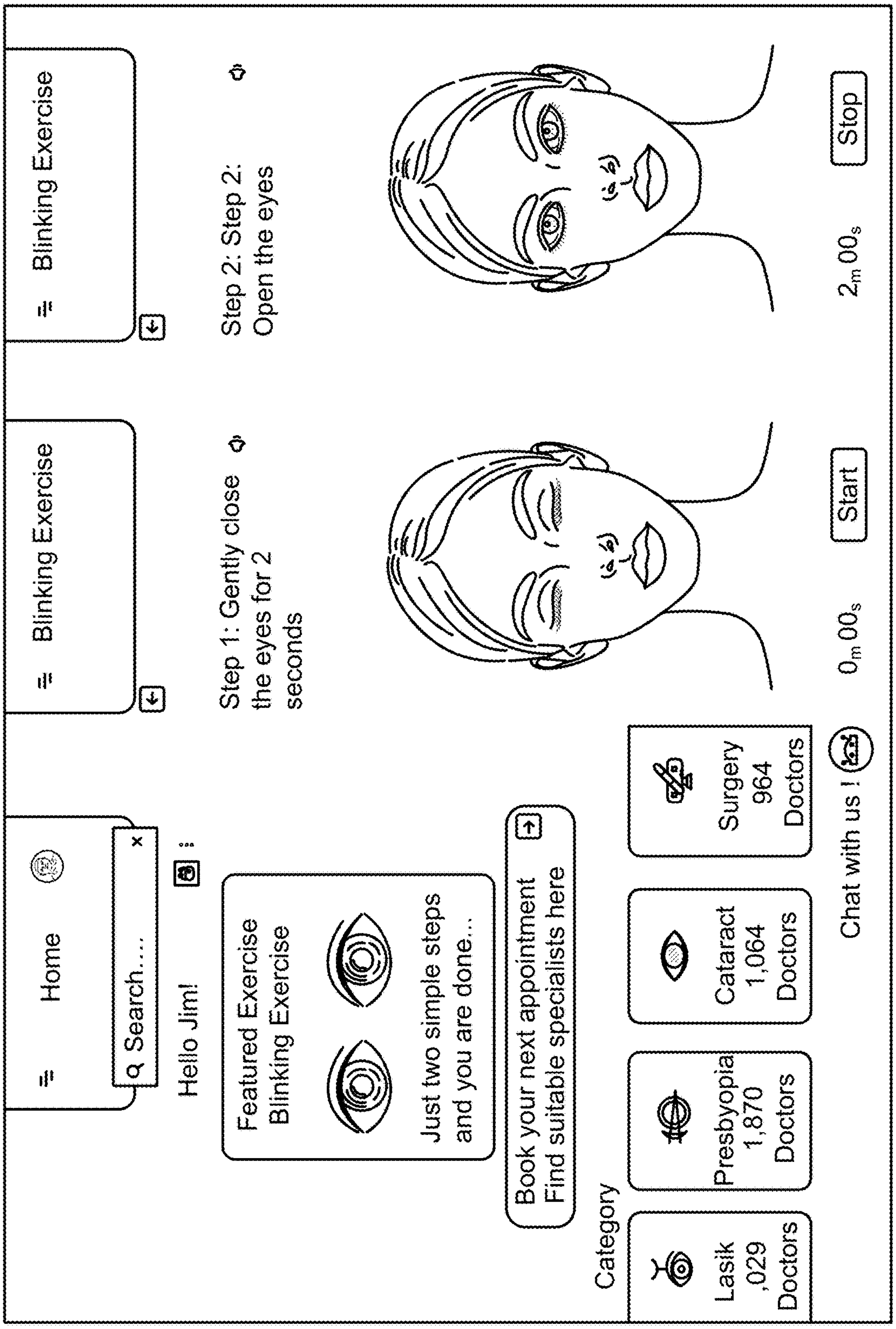
FIGS. 17D and 17E depicts an example of the method in which a patient would partake in the blinking exercise.
Figure 17E:
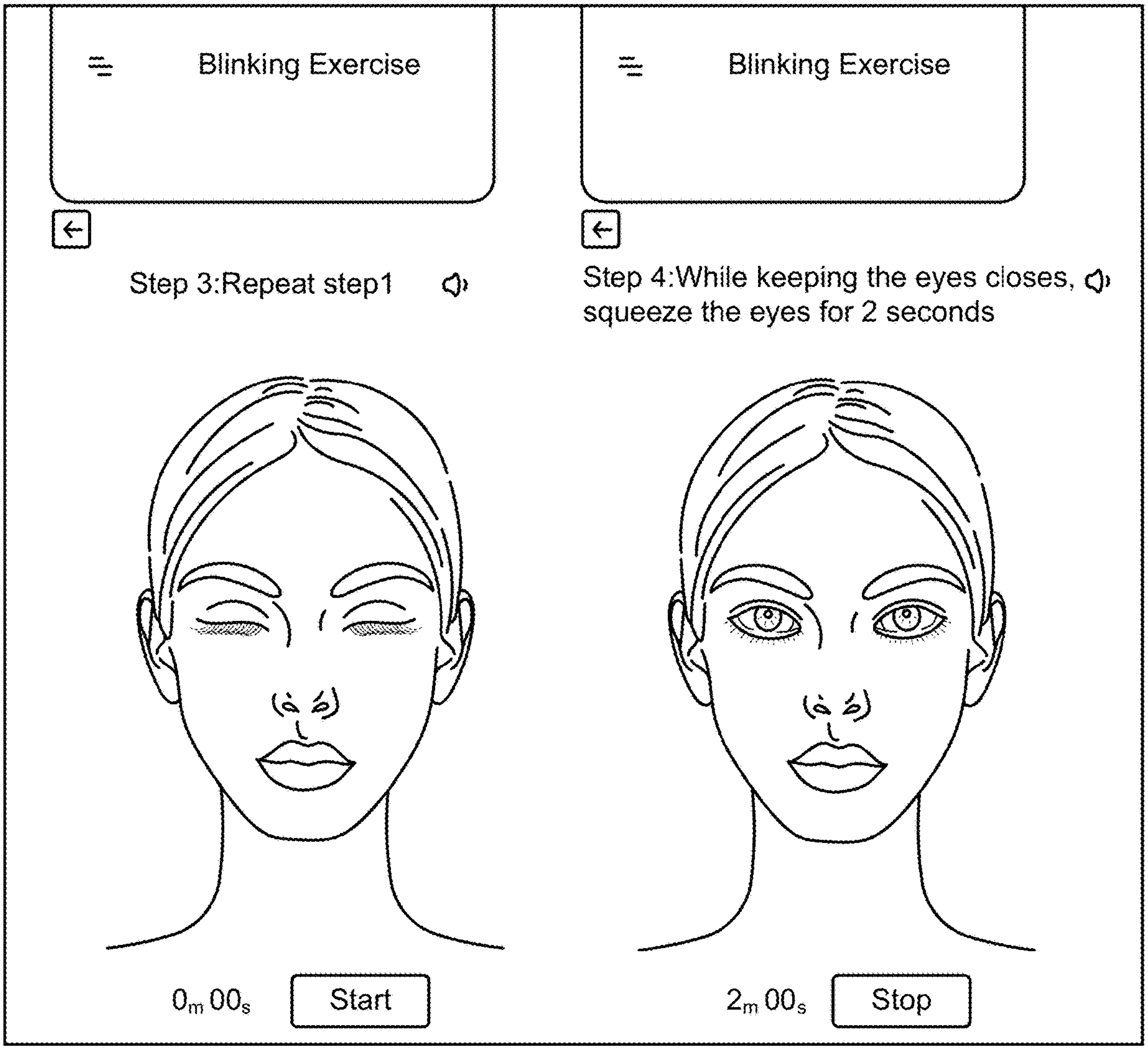

FIGS. 17D and 17E depicts an example of the method in which a patient would partake in the blinking exercise. This is done by evaluating the potential for prescribed patient blinking exercises in retaining and modifying blink patterns to alleviate dry eye symptoms and improve clinical signs. An example of the method is as shown.

Figure 17F:
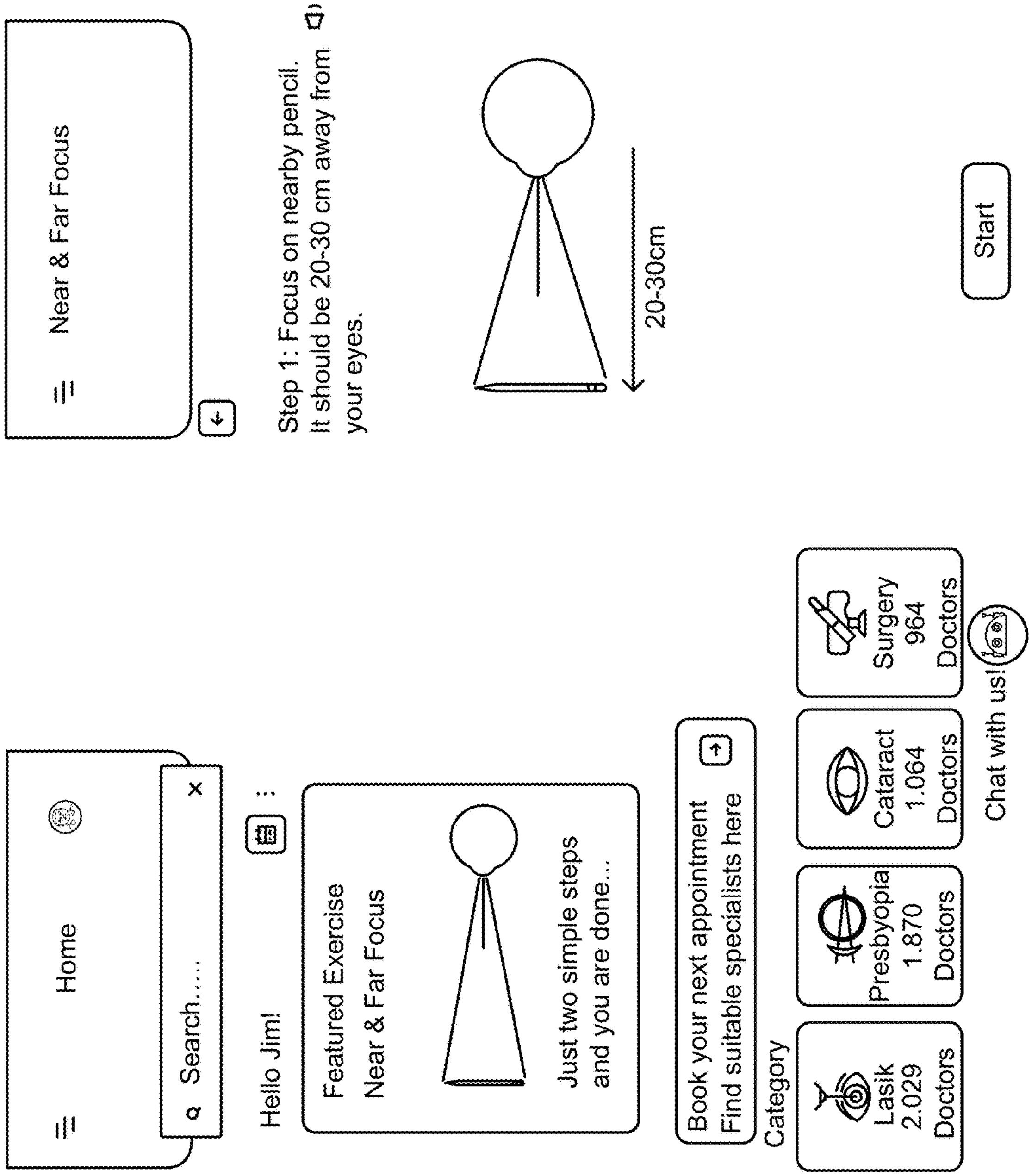
FIGS. 17F and 17G depict an example of the method in which a patient would partake in the near and far focus exercise.
Figure 17G:
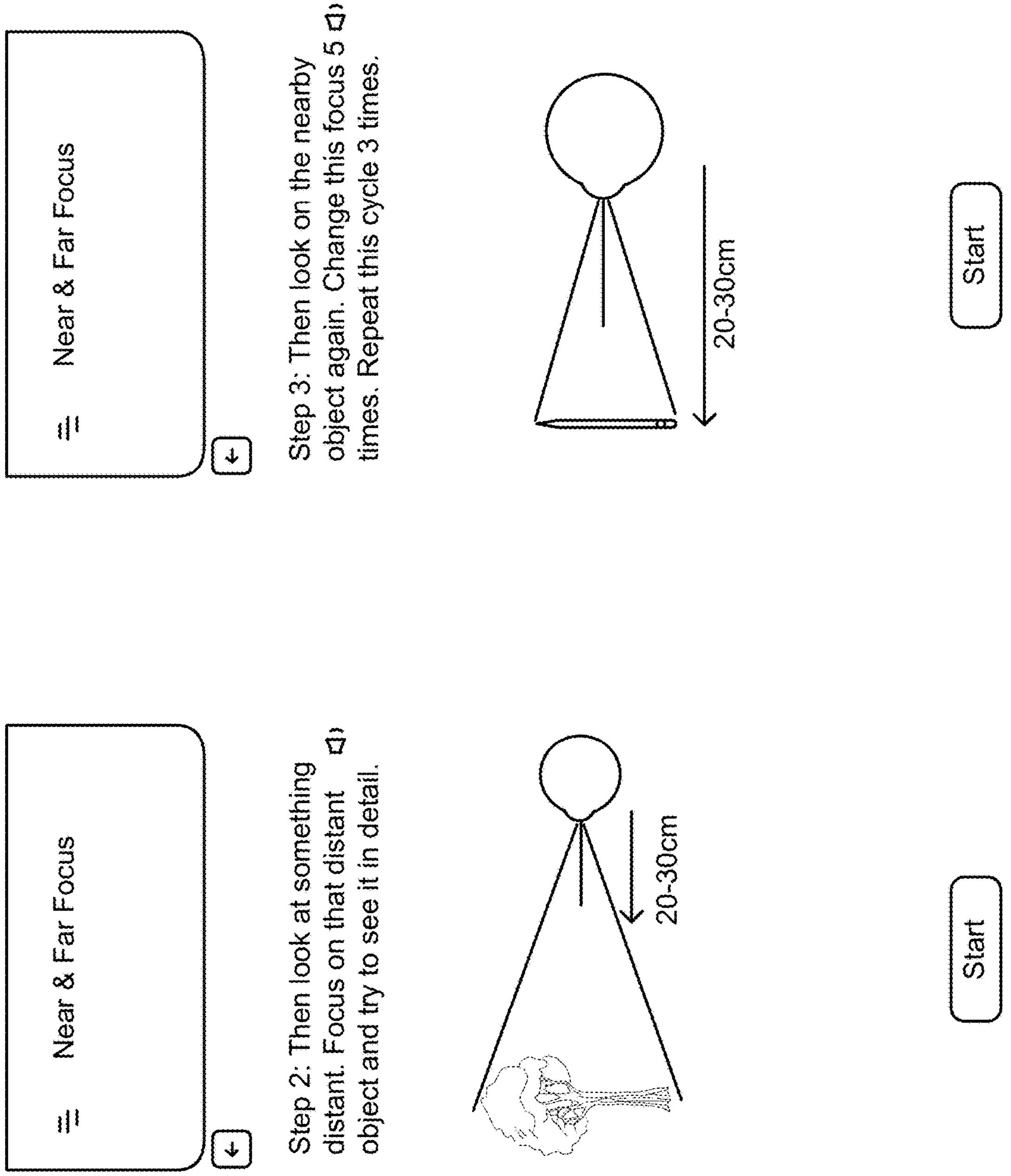

FIGS. 17F and 17G depict an example of the method in which a patient would partake in the near and far focus exercise. As shown, this would be done by the patient to focus on a nearby object, e.g., a pencil. It can be 20-30 cm away from their eyes, looking at something distant, focusing on the distant object, and attempting to see the object in detail. Then, looking at the nearby object again. The patient will adjust the focus 5 times and repeat the cycle up to 3 times for a physical workout of the mechanism of accommodation in the human eye.

Figure 18:
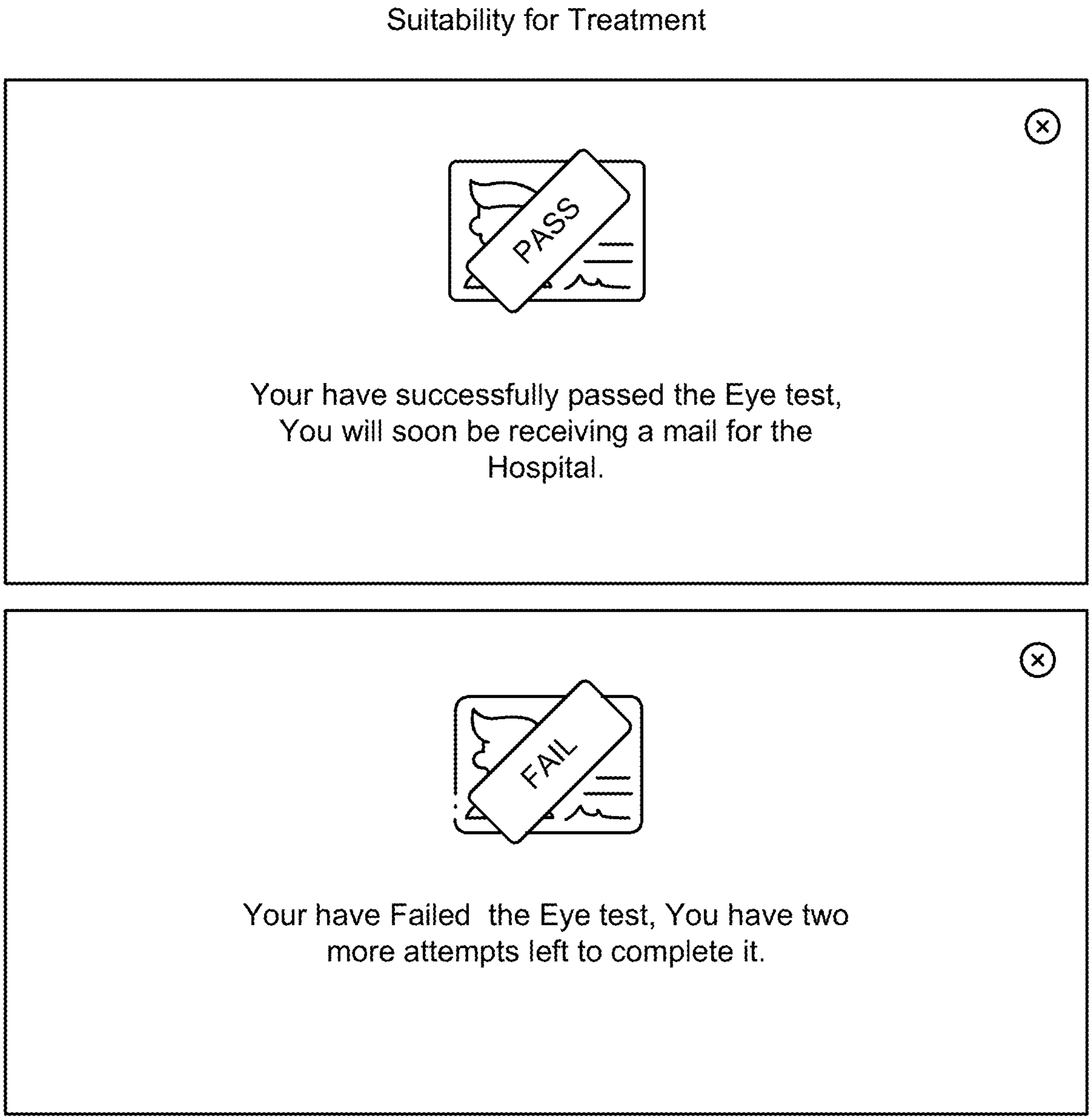
FIG. 18 depicts an example virtual assistant application treatment suitability user interface, in accordance with some example implementations.

FIG. 18 depicts an example virtual assistant application treatment suitability user interface, in accordance with some example implementations. As shown, a user may pass or fail a vision or eye test and may be shown at least one of the images in the example of FIG. 18.

FIGS. 19A, 19B, 19C, 19D, 19E, and 19F depicts an example virtual assistant application home screen and navigation user interfaces, in accordance with some example implementations. As shown, a home scream of the virtual assistant application may include an exercises tab, a surgery status tab, and a final report tab. The home screen may also provide settings for the application.

Figure 19A:
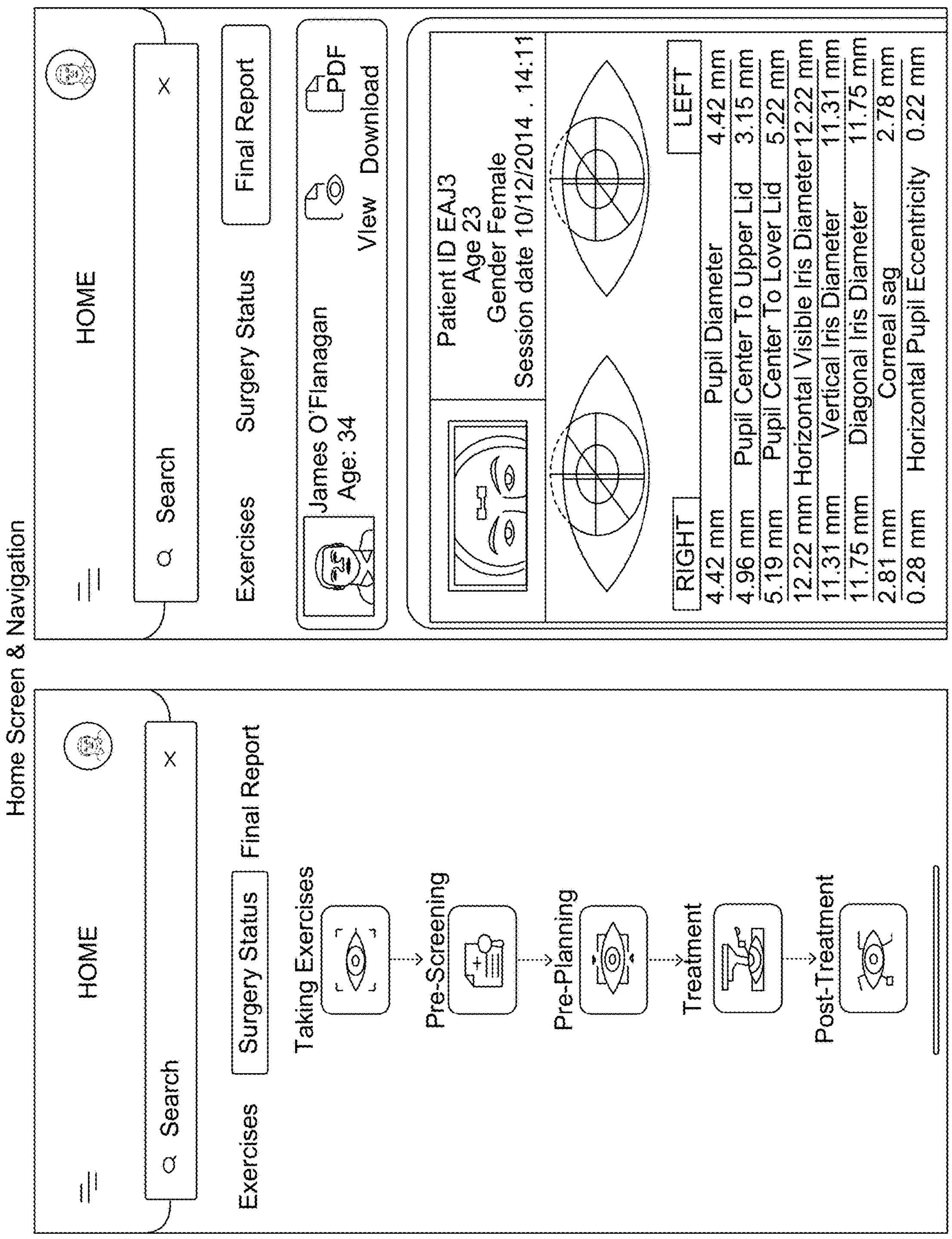
Figure 19B:
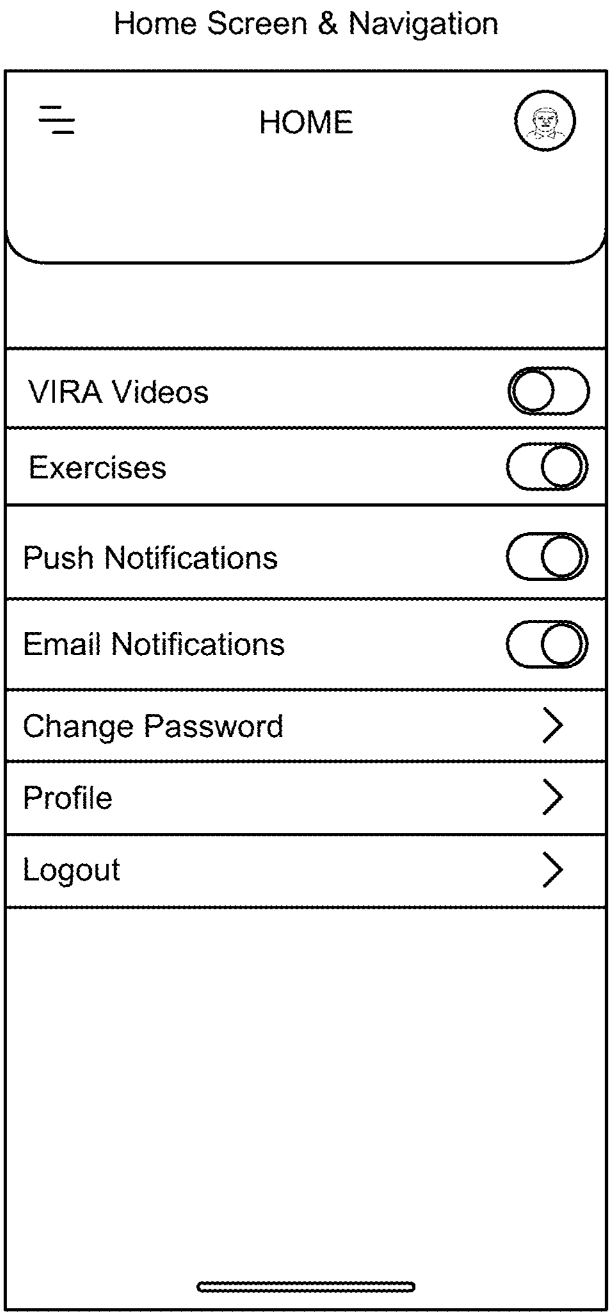
Figure 19C:
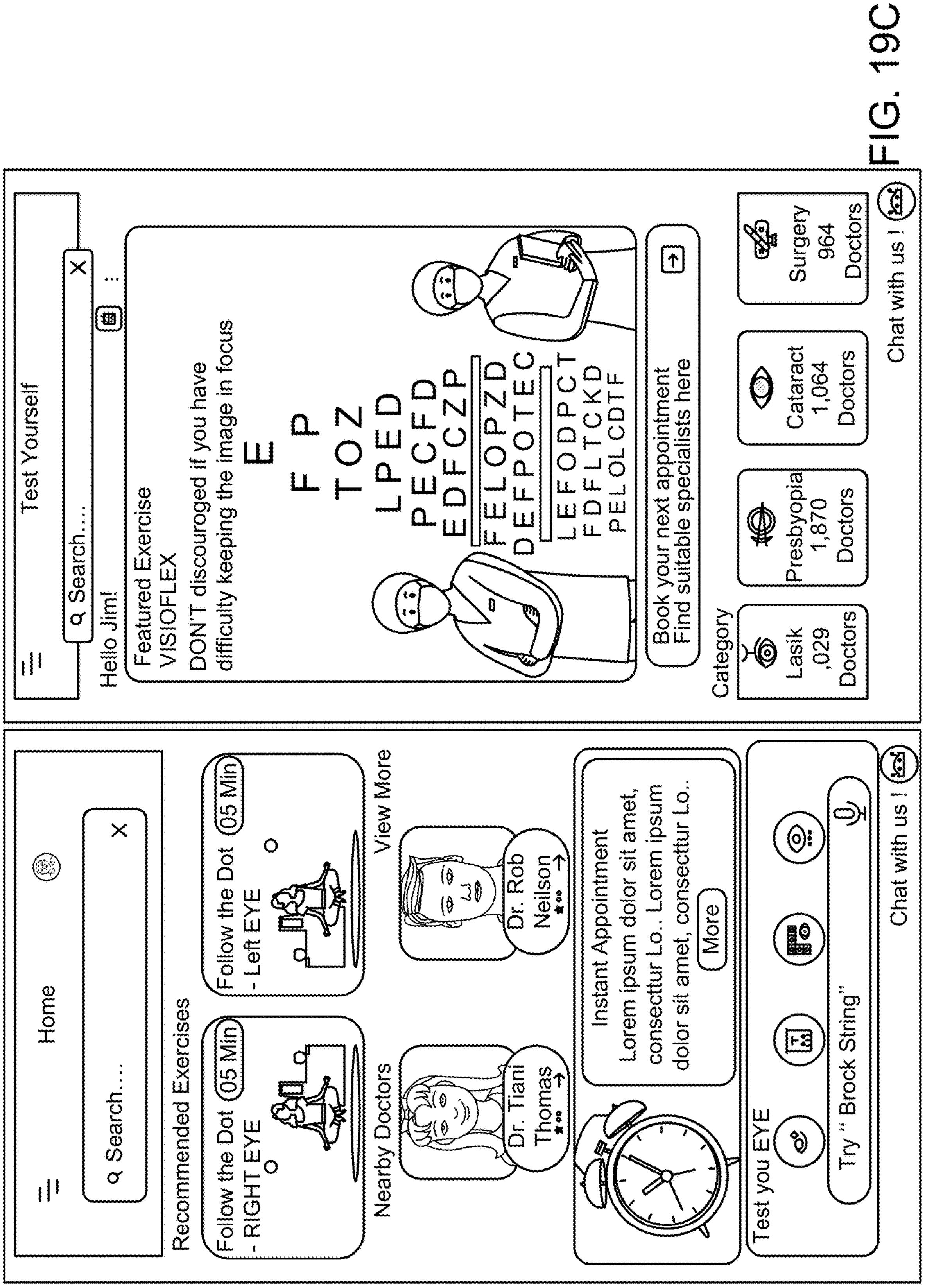
Figure 19E:
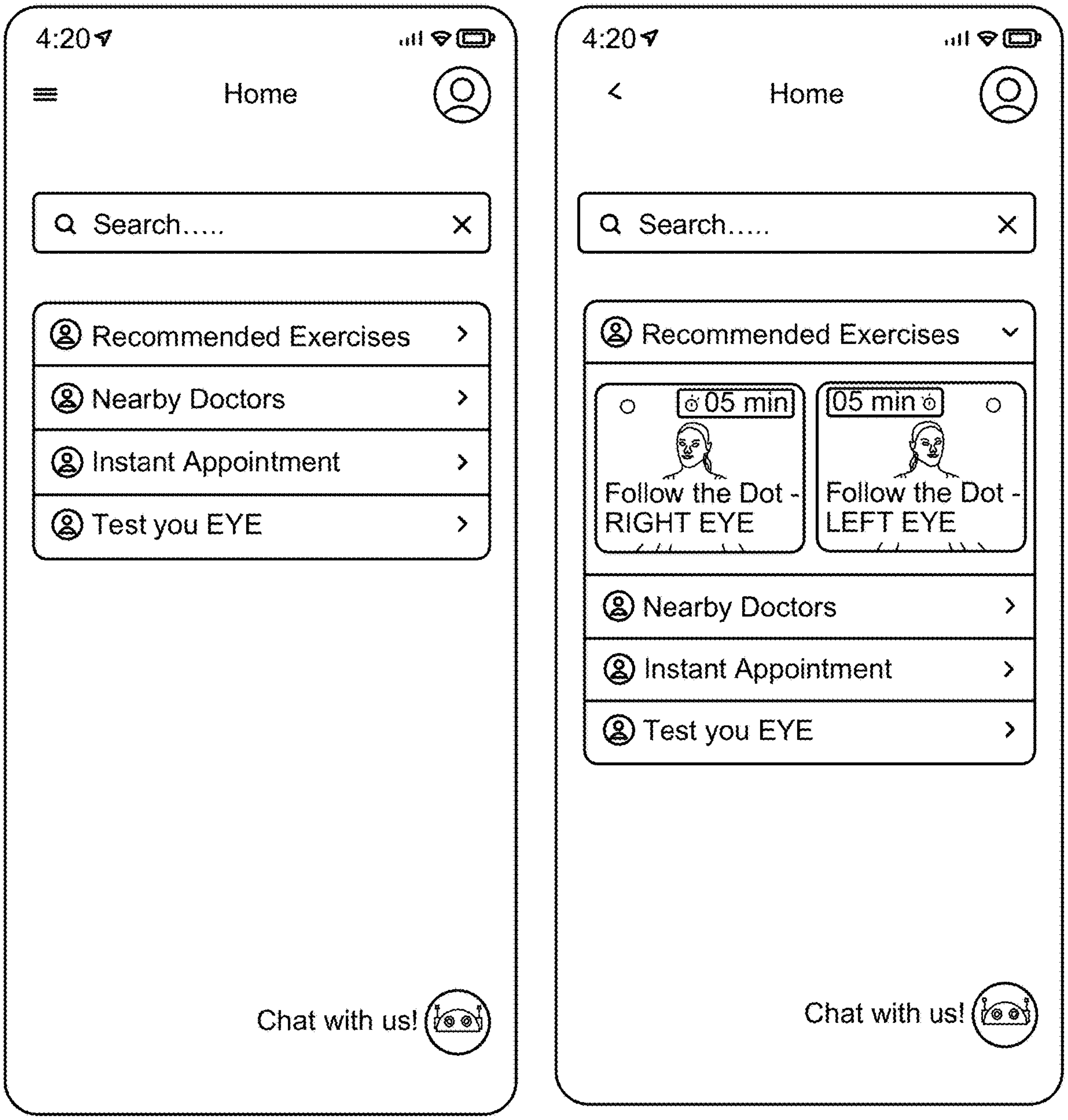
Figure 19F:
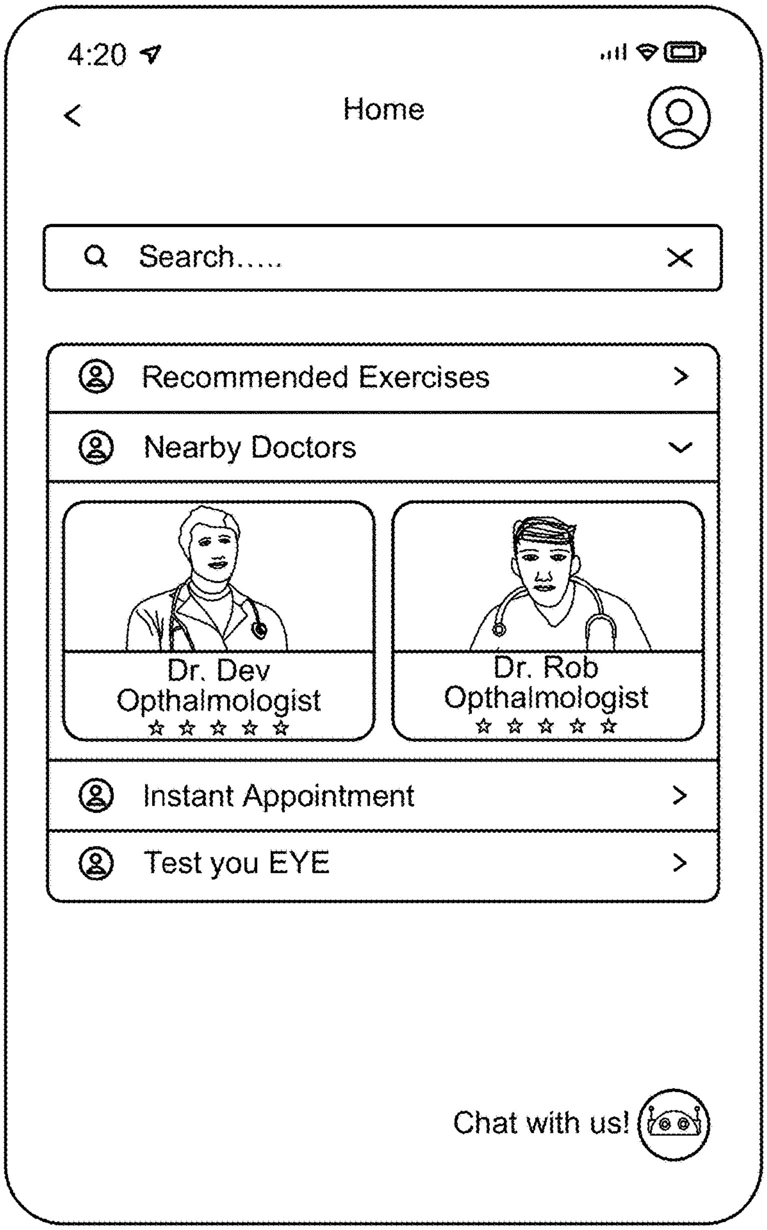
Figure 19G:
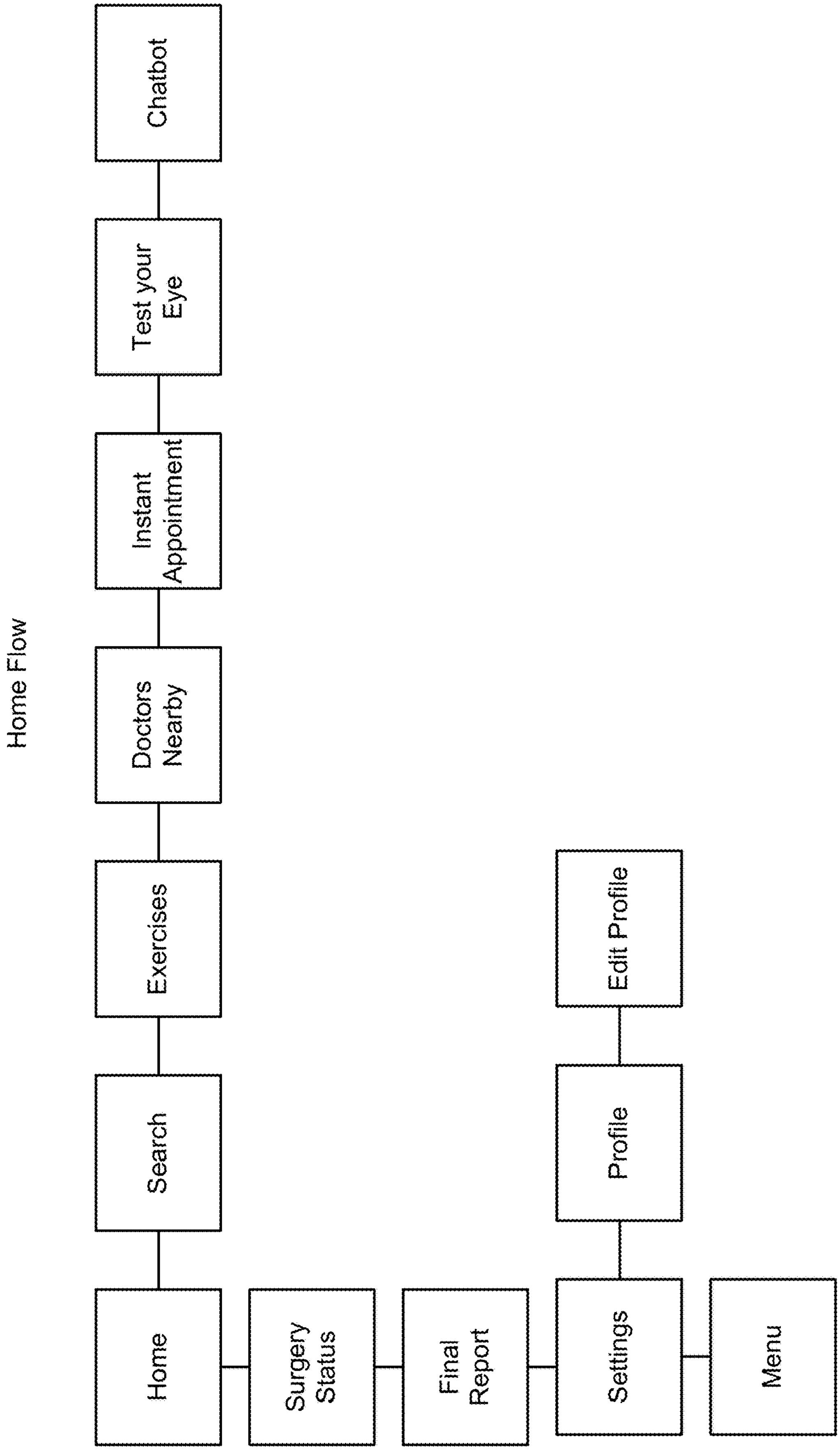
FIG. 19G depicts an example in which the application's home feature flow.

FIG. 19G depicts an example in which the application's home feature will flow. As shown, the flow pages consist of but are not limited to, search, exercises, nearby doctors, scheduling an appointment, testing your eye, chatbot, surgery status, final report, settings, patient profile, and hamburger menu.

Figure 19H:
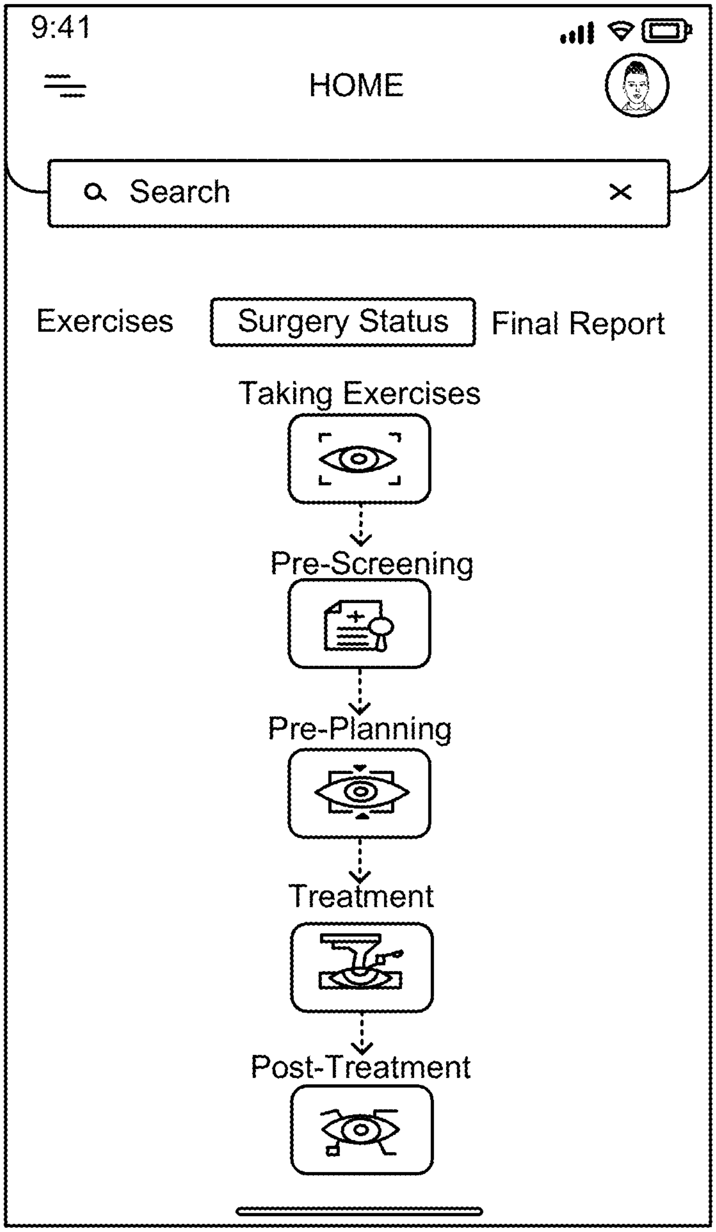
FIGS. 19H and 19I depicts an example of the surgery status tab, and the final report tab.
Figure 19I:
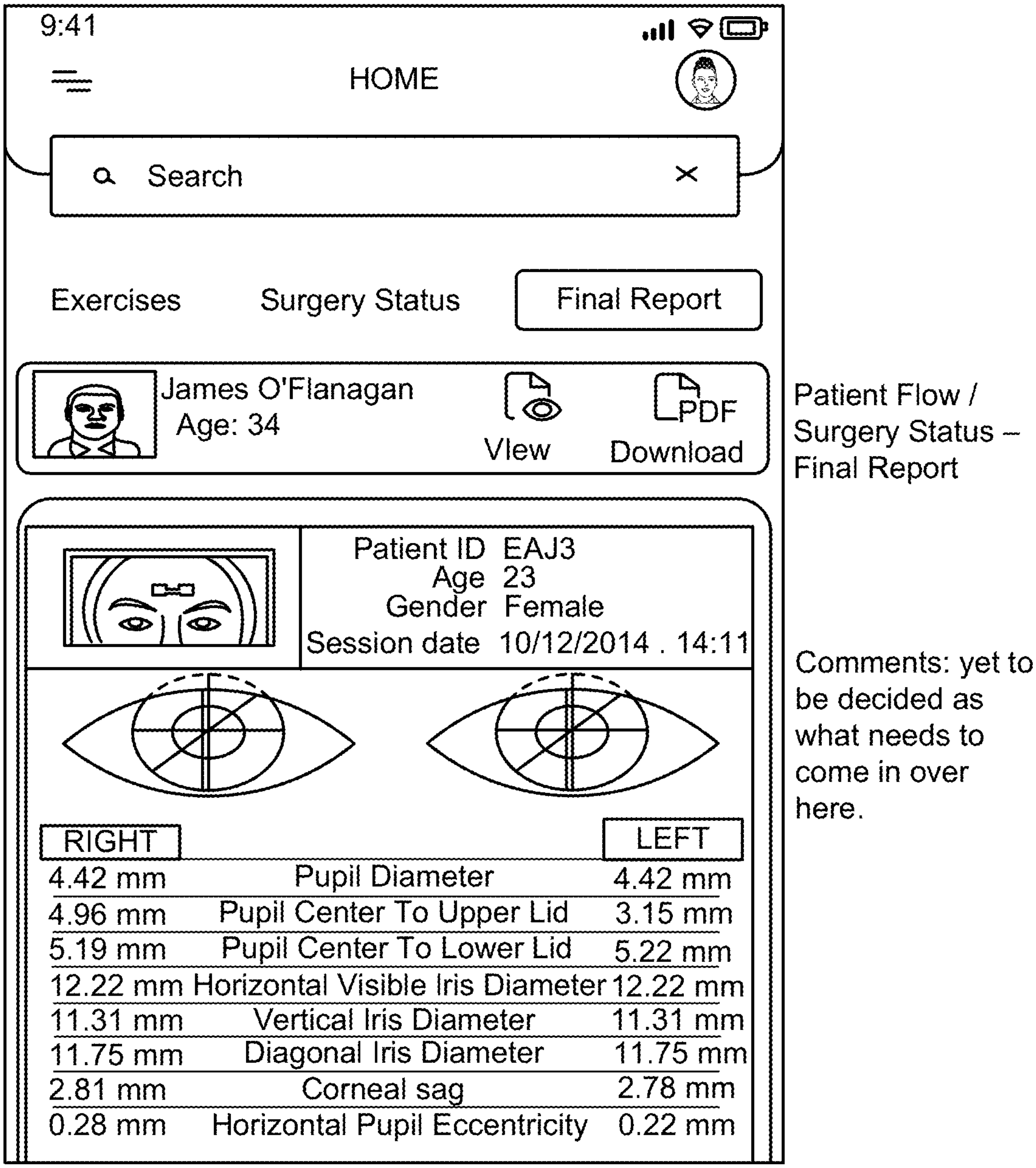

FIGS. 19H and 19I depicts an example of the surgery status tab, and the final report tab. The surgery status tab remains synchronous with the patient towards the current phase of a given procedure. Whether the patient is training on exercises, going into the clinic for pre-screening and pre-planning, undergoing treatment, and going into the clinic for post-treatment analysis. The final report tab will lay out results from a surgical treatment with datapoints and graphs depicting potential visual improvement.

Figure 20:
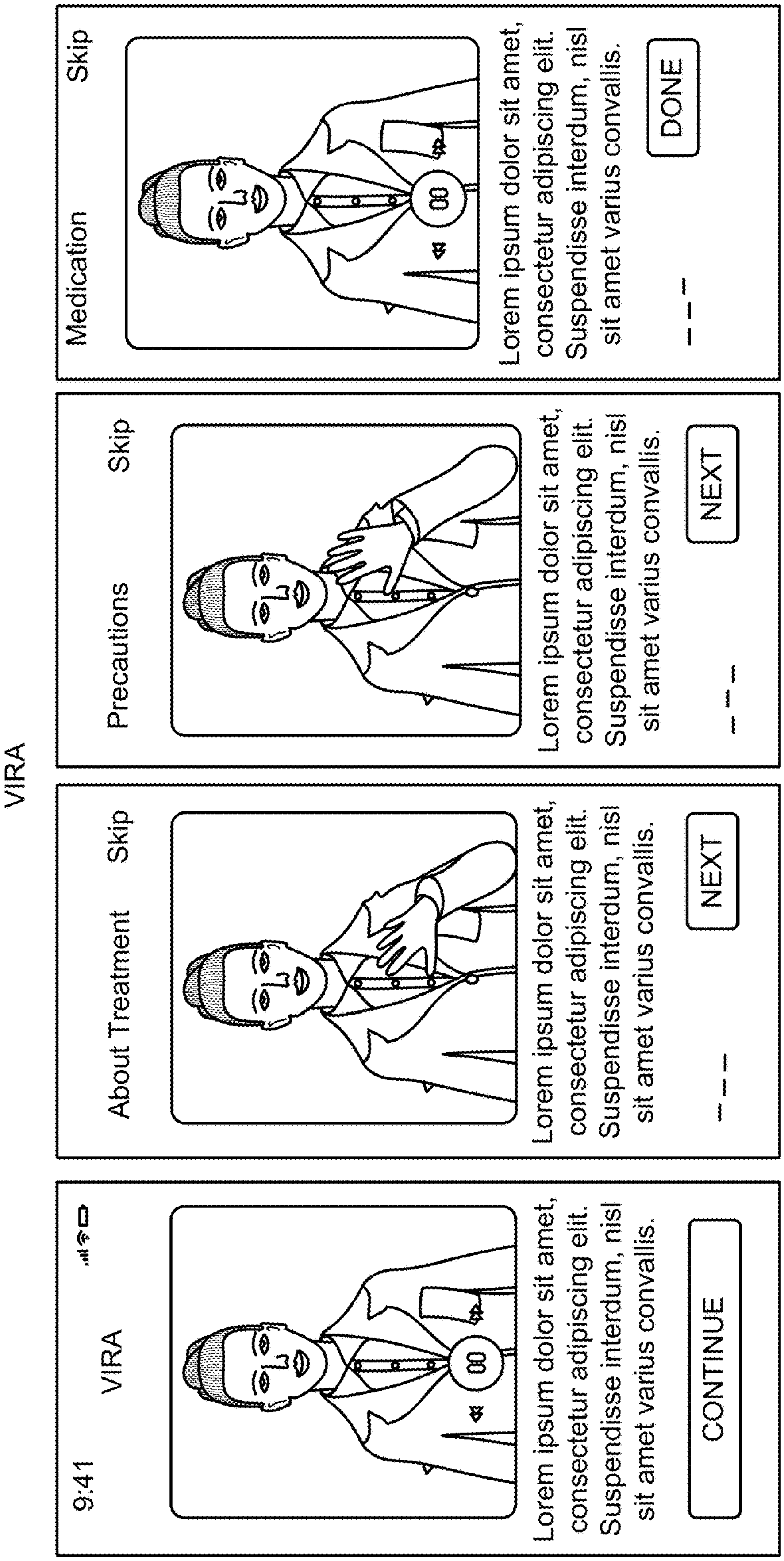
FIG. 20 depicts an example virtual assistant application user interfaces, in accordance with some example implementations.

FIG. 20 depicts an example, virtual assistant application user interfaces, in accordance with some example implementations. As shown, the virtual assistant application may provide information about a treatment, precautions regarding the treatment, and medications associated with the treatment.

Figure 21:
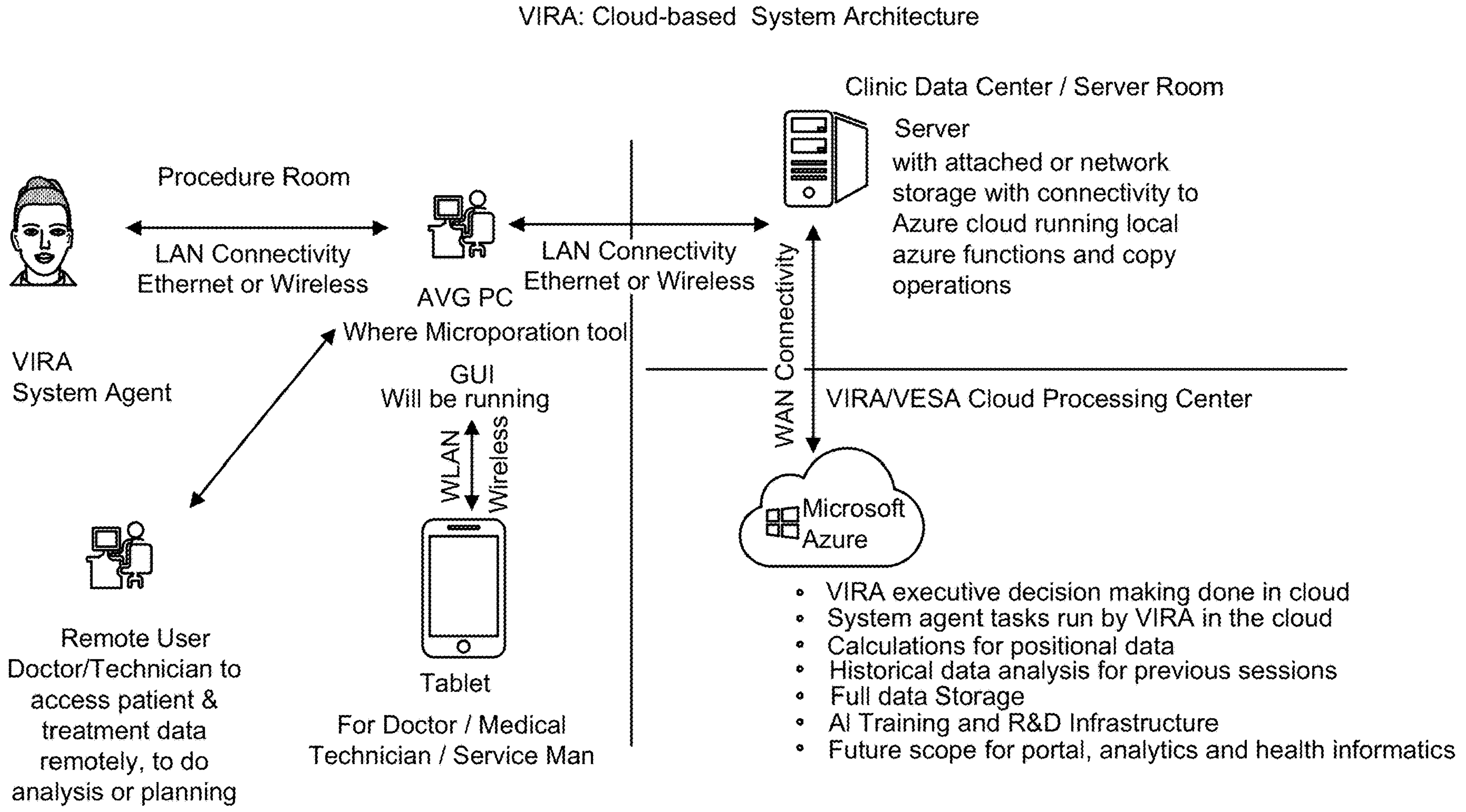
FIG. 21 depicts an example virtual assistant application cloud based system architecture, in accordance with some example implementations.

FIG. 21 depicts an example virtual assistant application cloud based system architecture, in accordance with some example implementations. As shown, a cloud processing center may control executive decisions of VIRA, perform system agent tests run by VIRA in the cloud, perform calculations for positional data, perform historical data analysis for previous sessions, provide full data storage, provide artificial intelligence training and research and development infrastructure, and provide analytics and health informatics.

Figure 22:
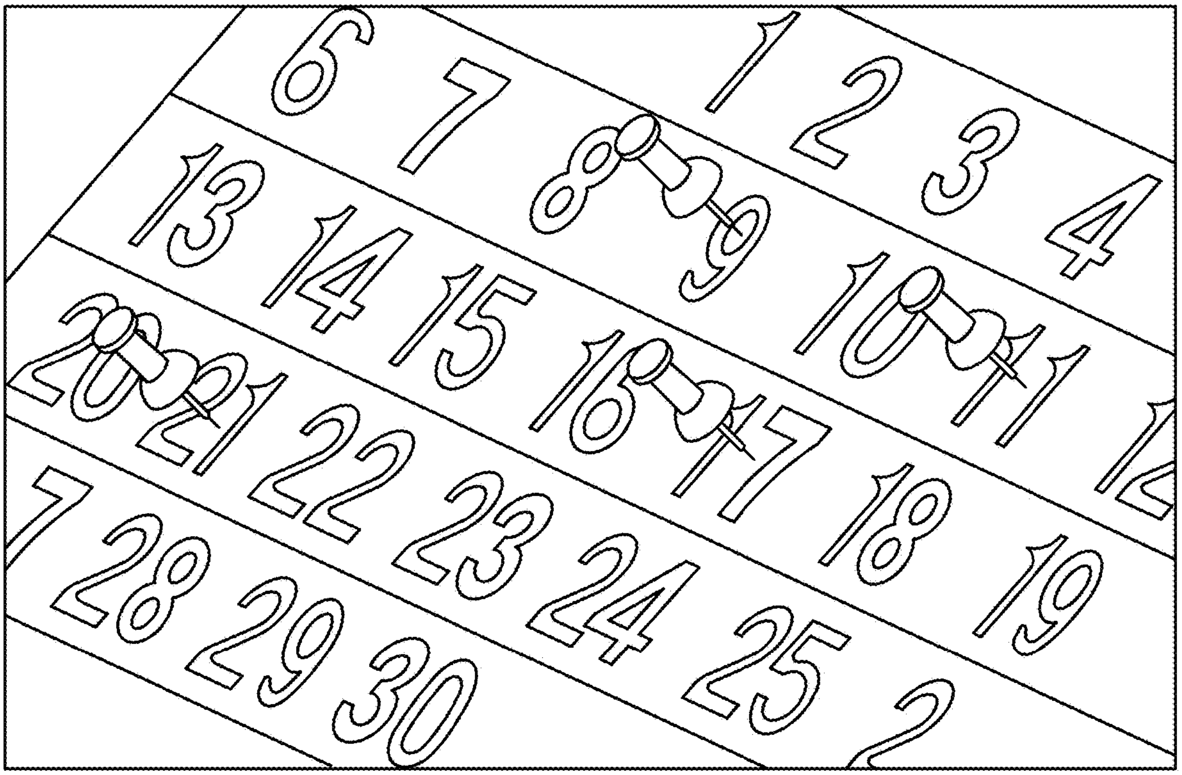
FIG. 22 depicts an example virtual assistant application scheduling agent, in accordance with some example implementations.
Figure 25:
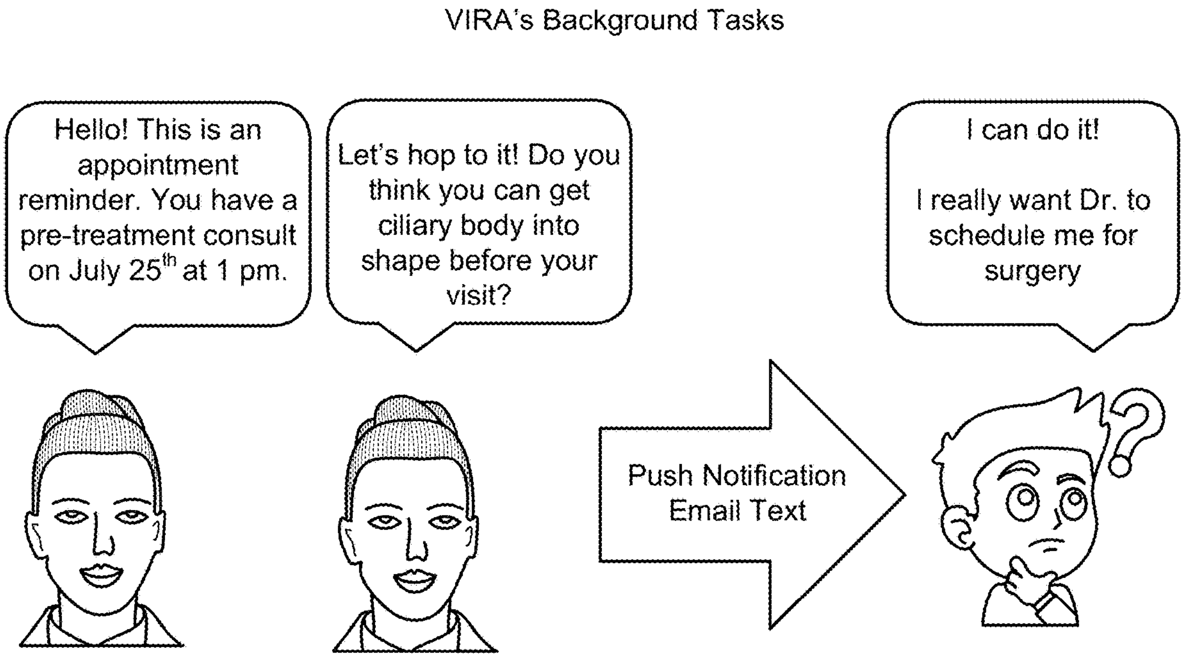
FIG. 25 depicts example virtual assistant application background tasks, in accordance with some example implementations.
Figure 26:
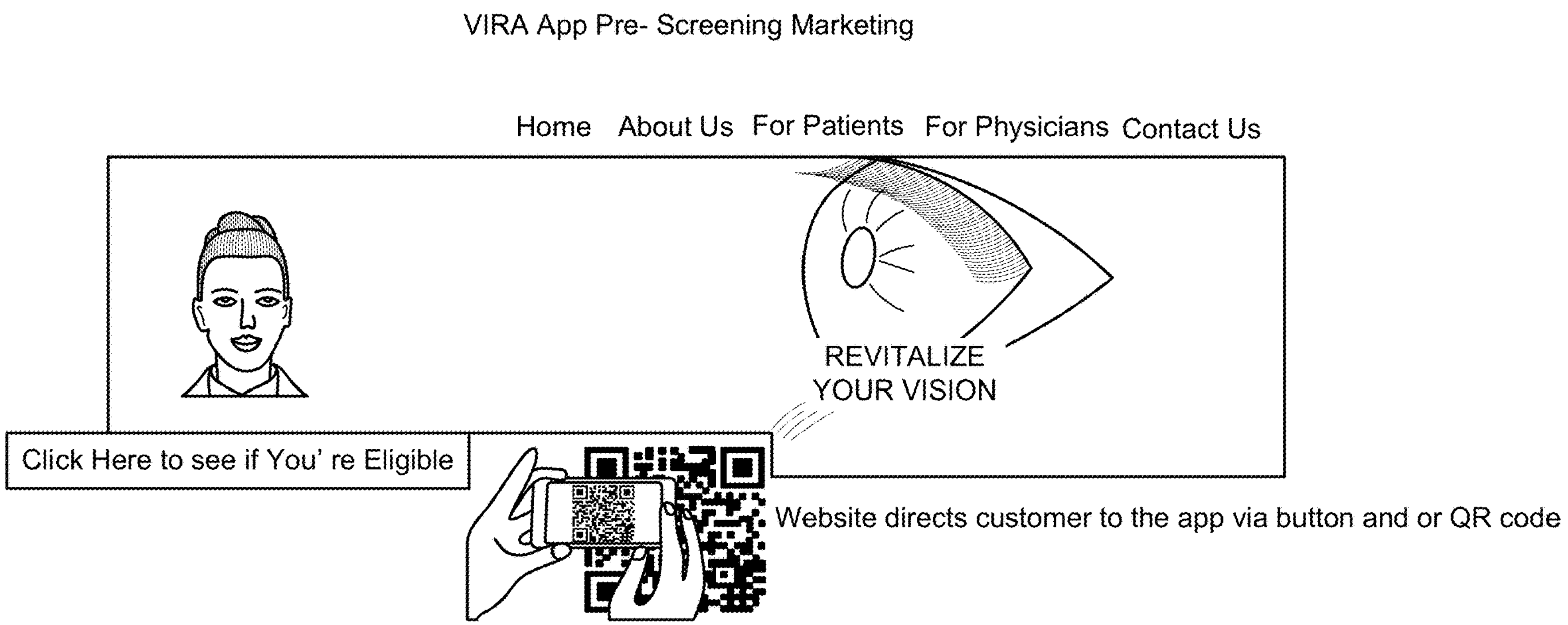
FIG. 26 depicts an example virtual assistant application user pre-screening, in accordance with some example implementations.

FIG. 22 depicts an example virtual assistant application scheduling agent, in accordance with some example implementations. In some aspects, the virtual assistant application scheduling agent may create events in the calendar of the patient, doctor, doctor's office, or the like. FIG. 25 depicts an example virtual assistant application background tasks, in accordance with some example implementations. FIG. 26 depicts an example virtual assistant application user prescreening, in accordance with some example implementations.

Figure 23:
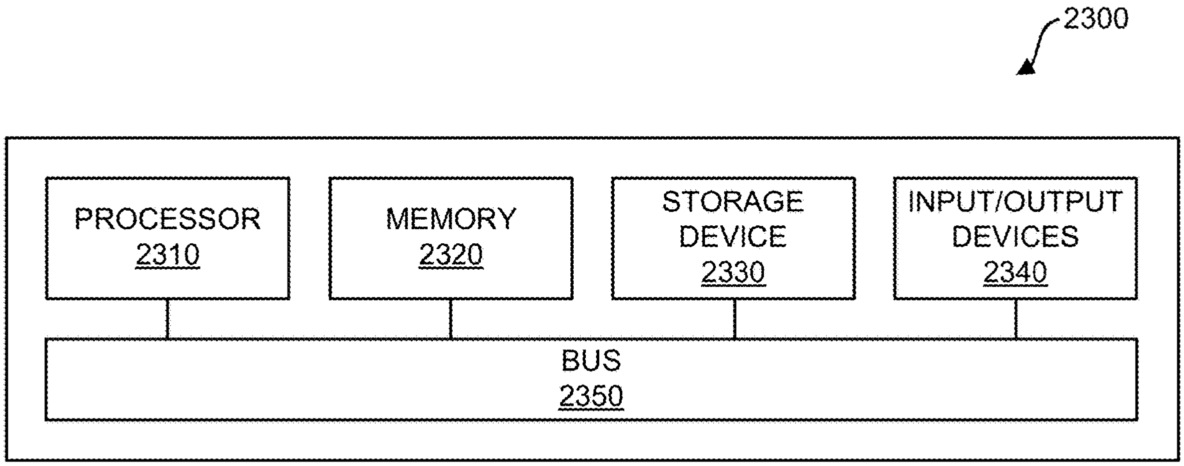
FIG. 23 depicts a block diagram of an example computing apparatus, in accordance with some example implementations.

FIG. 23 illustrates an example computing apparatus 2300 which may be used to implement one or more of the described devices and/or components, in accordance with some example implementations. For example, at least a portion of the computing apparatus 2300 may be used to implement at least a portion of a client device, a server, a processor, or the like. Computing apparatus 2300 may perform one or more of the processes described herein.

As illustrated, computing apparatus 2300 may include one or more processors such as processor 2310 to execute instructions that may implement operations consistent with those described herein. Apparatus 2300 may include memory 2320 to store executable instructions and/or information. Memory 2320 may include solid-state memory, solid-state disk drives, magnetic disk drives, or any other information storage device. In some aspects, the memory 2320 may provide storage for at least a portion of a database. Apparatus 2300 may include input/output devices 2340 to a wired network or a wireless network. Wireless networks may include, but are not limited to: radio antenna, WiFi, WiMax, WAN, WAP Bluetooth, satellite, and cellular networks (2G/3G/4G/5G), and/or any other wireless network. In order to effectuate wireless communications, the input/output devices 2340, for example, may utilize one or more antennas.

Apparatus 2300 may include one or more user interfaces, such as graphical user interface 1100. The user interface can include hardware or software interfaces, such as a keyboard, mouse, or other interface, some of which may include a touchscreen integrated with a display. The display may be used to display information such as promotional offers or current inventory, provide prompts to a user, receive user input, and/or the like. In various implementations, the user interface can include one or more peripheral devices and/or the user interface may be configured to communicate with these peripheral devices.

In some aspects, the user interface may include one or more of the sensors described herein and/or may include an interface to one or more of the sensors described herein. The operation of these sensors may be controlled at least in part by a sensor module. The apparatus 2300 may also comprise and input and output filter, which can filter information received from the sensors or other user interfaces, received and/or transmitted by the network interface, and/or the like. For example, signals detected through sensors can be passed through a filter for proper signal conditioning, and the filtered data may then be passed to the processor 2310 for validation and processing (e.g., before transmitting results or an indication via the input/output devices 2340). The apparatus 2300 may be powered through the use of one or more power sources. As illustrated, one or more of the components of the apparatus 2300 may communicate and/or receive power through a system bus 2350.

Figure 24:
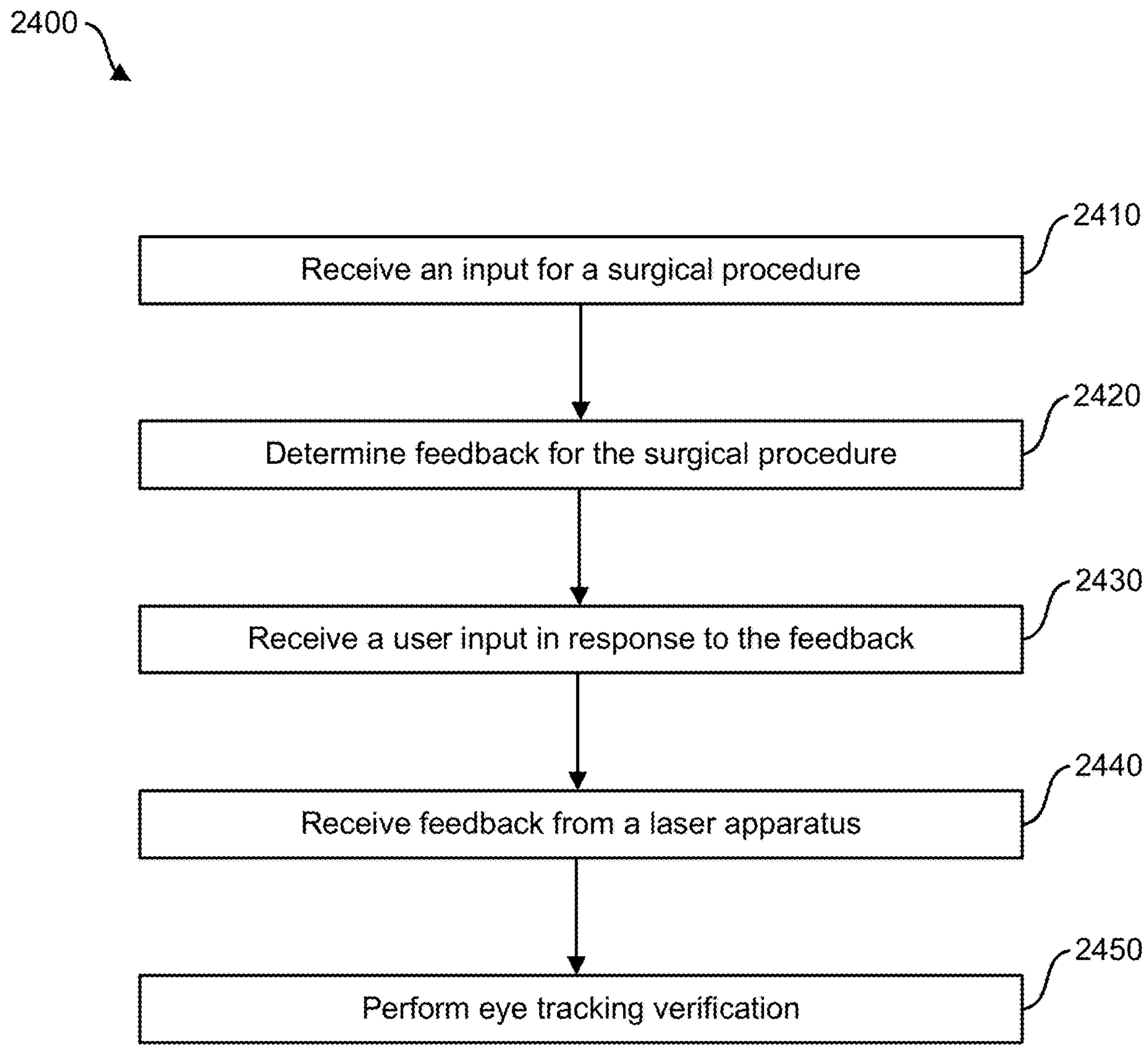
FIG. 24 depicts an example of a method for implementing a virtual integrated remote assistant, in accordance with some example implementations.

FIG. 24 illustrates a flowchart of a method for remote eye surgery training, in accordance with some example implementations. In various implementations, the method 2400 (or at least a portion thereof) may be performed by one or more of the laser apparatus 1025, the system 1000, the computing apparatus 2300, other related apparatuses, and/or some portion thereof.

Figure 27A:
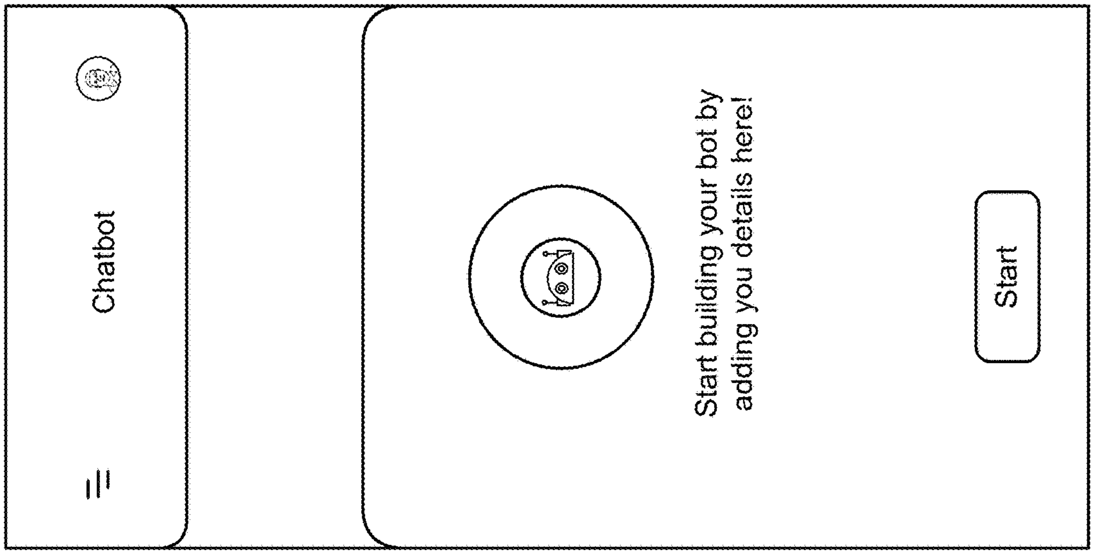
FIGS. 27A-27C depict an autonomous chatbot widget that connects patients to doctors as well as manages simple and complex tasks.
Figure 27B:
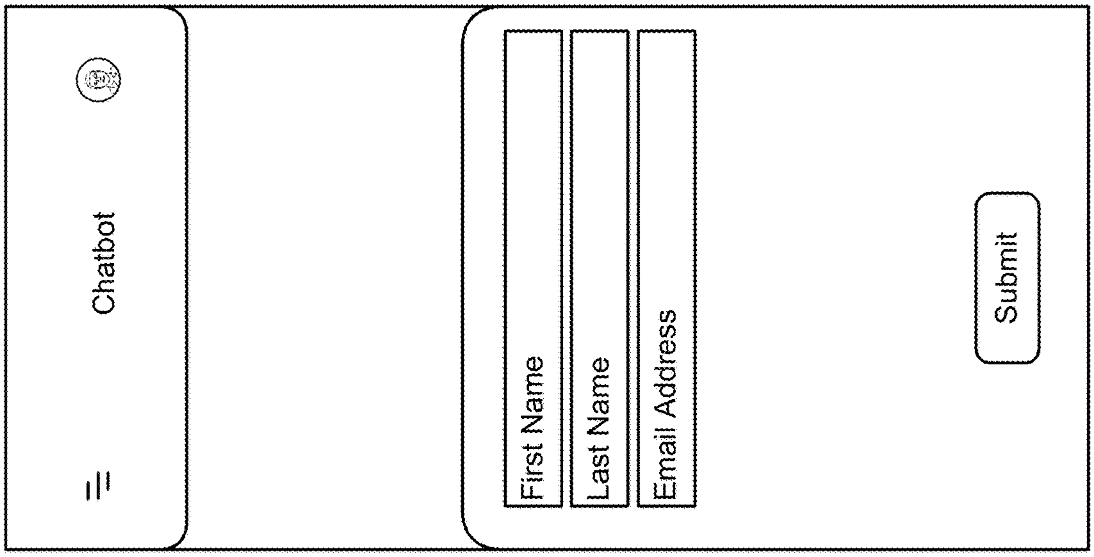
Figure 27C:
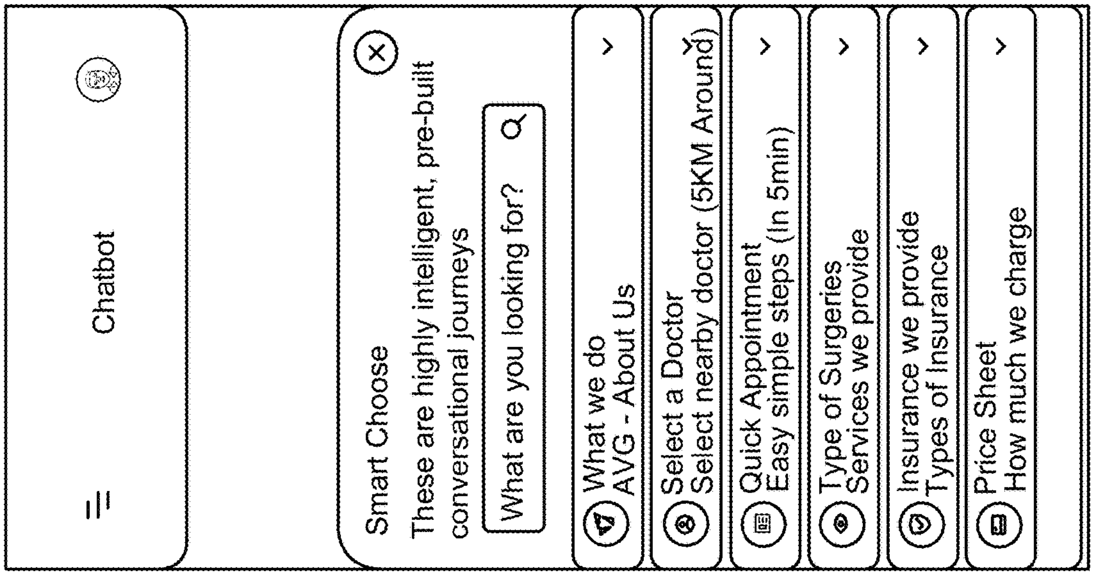
Figure 28A:
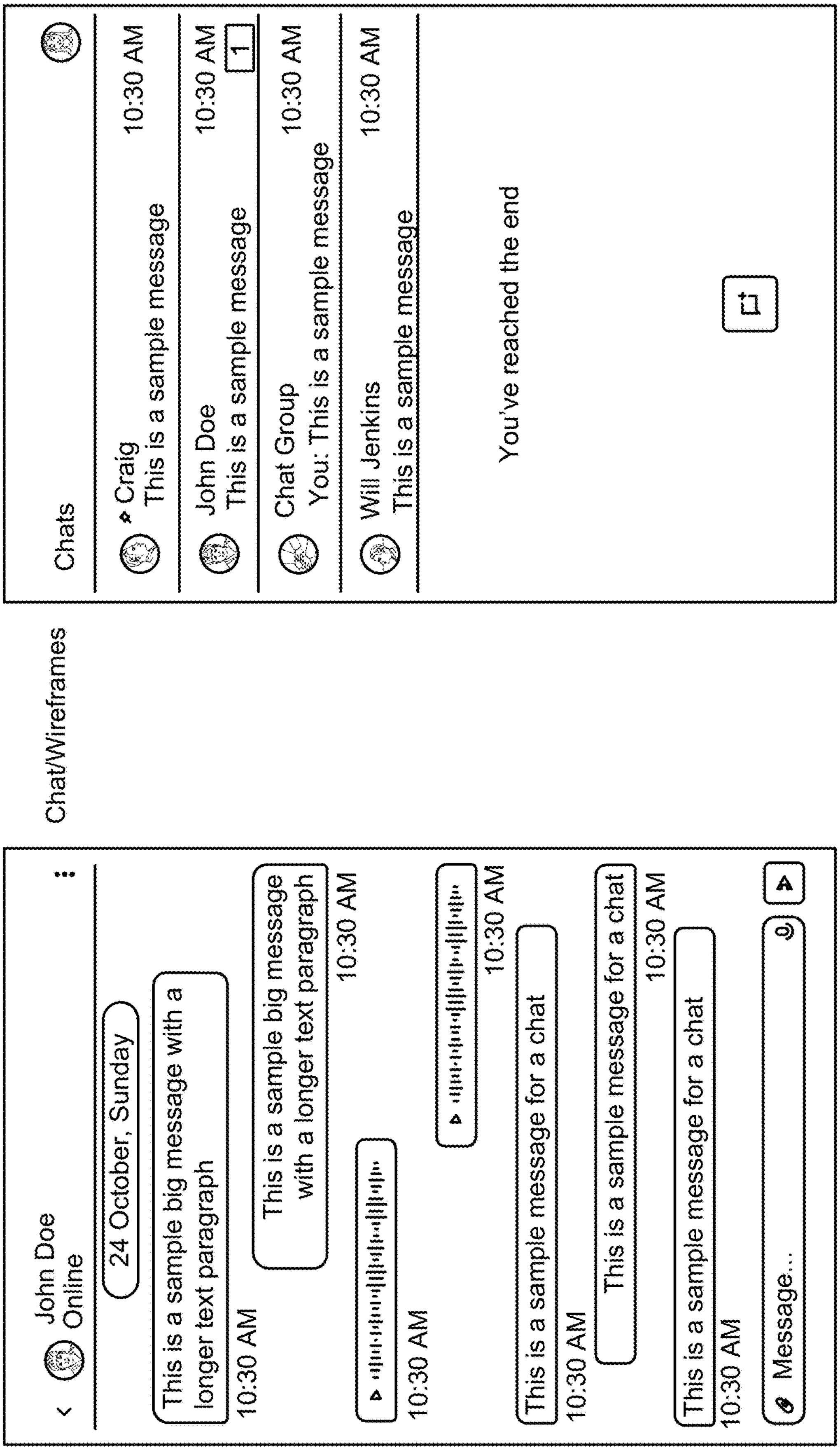
FIGS. 28A-28B depict a chat feature.
Figure 28B:
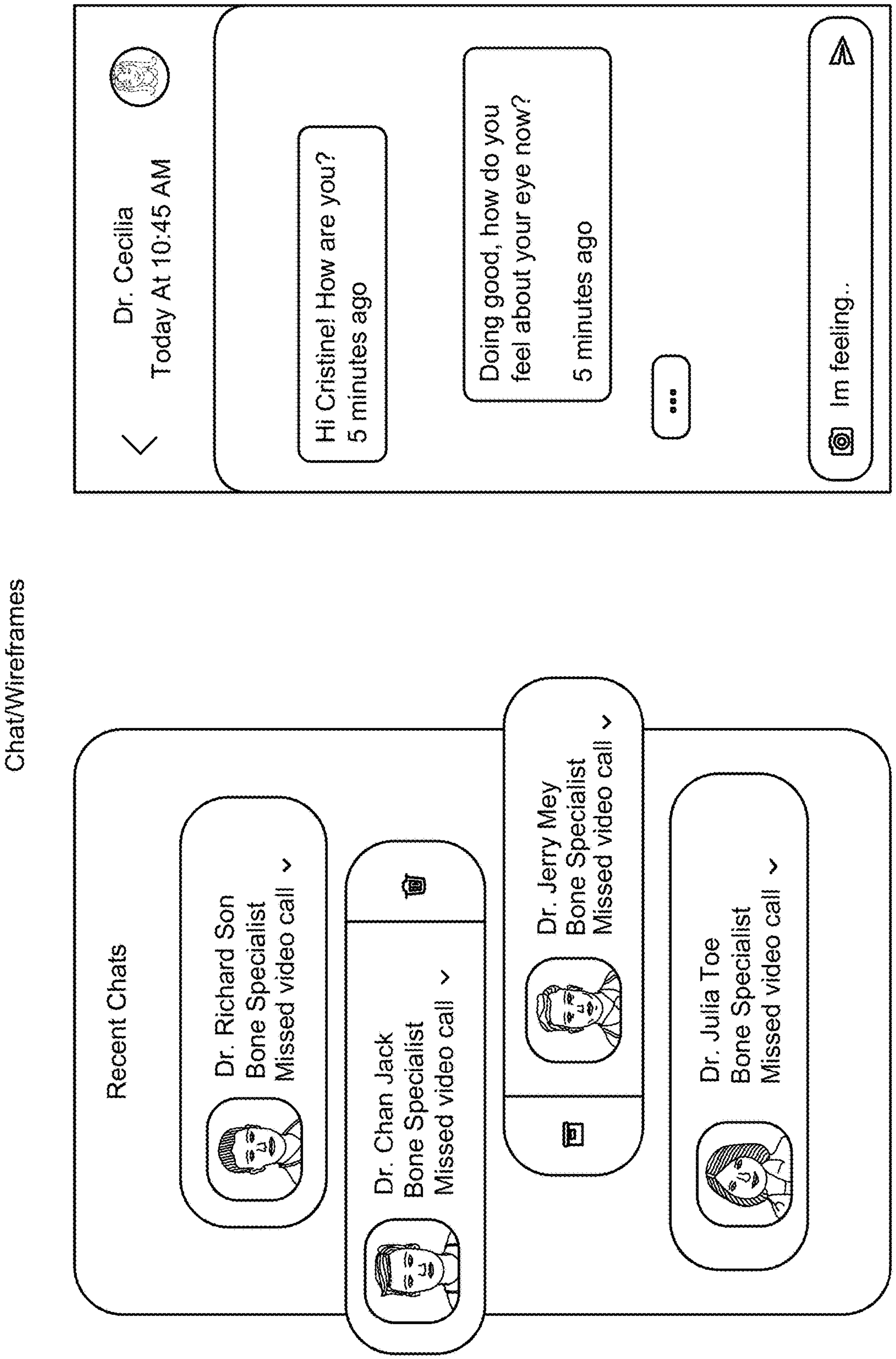
Figure 29A:
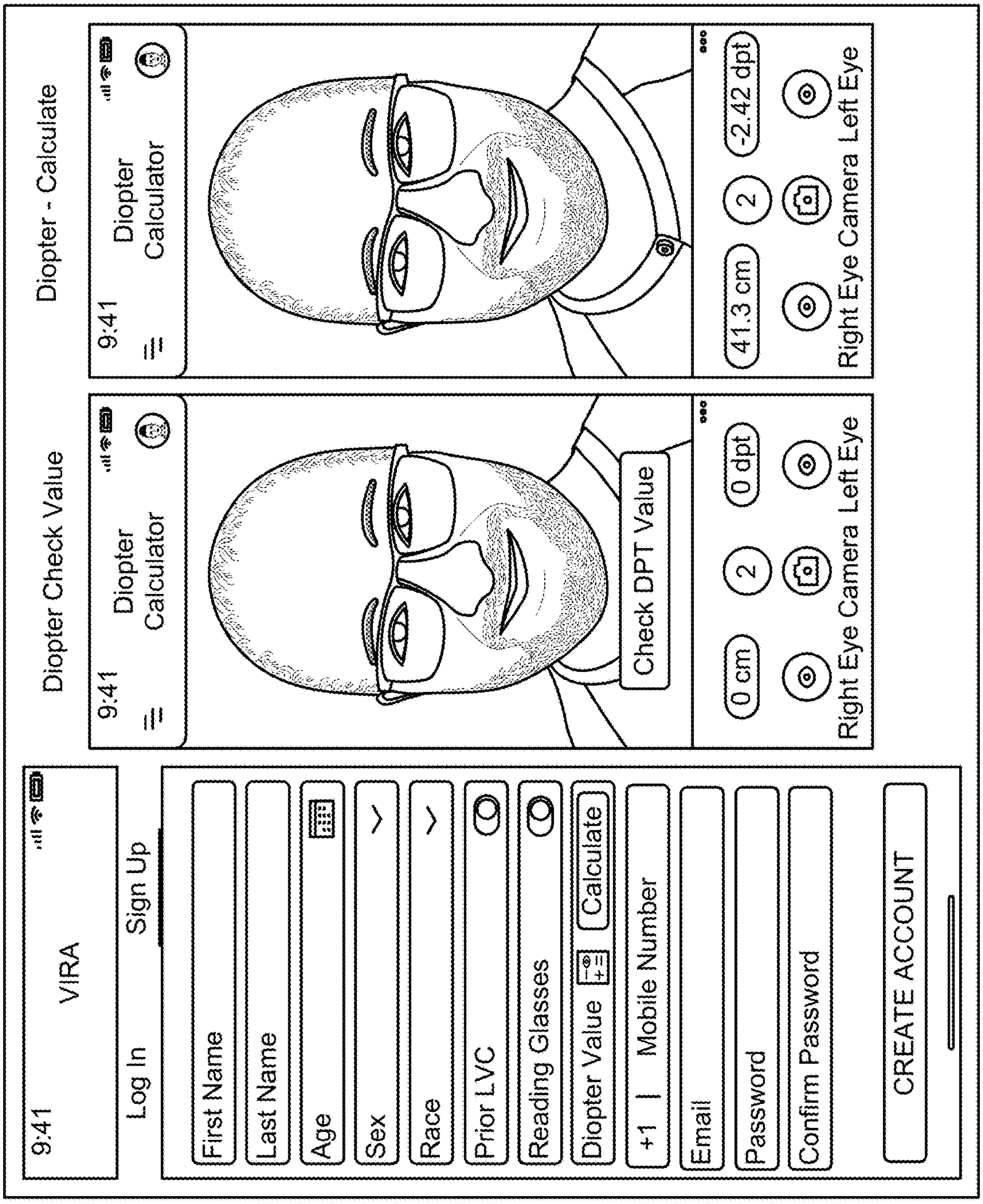
FIGS. 29A and 29B show example evaluation upon sign up feature.
Figure 29B:
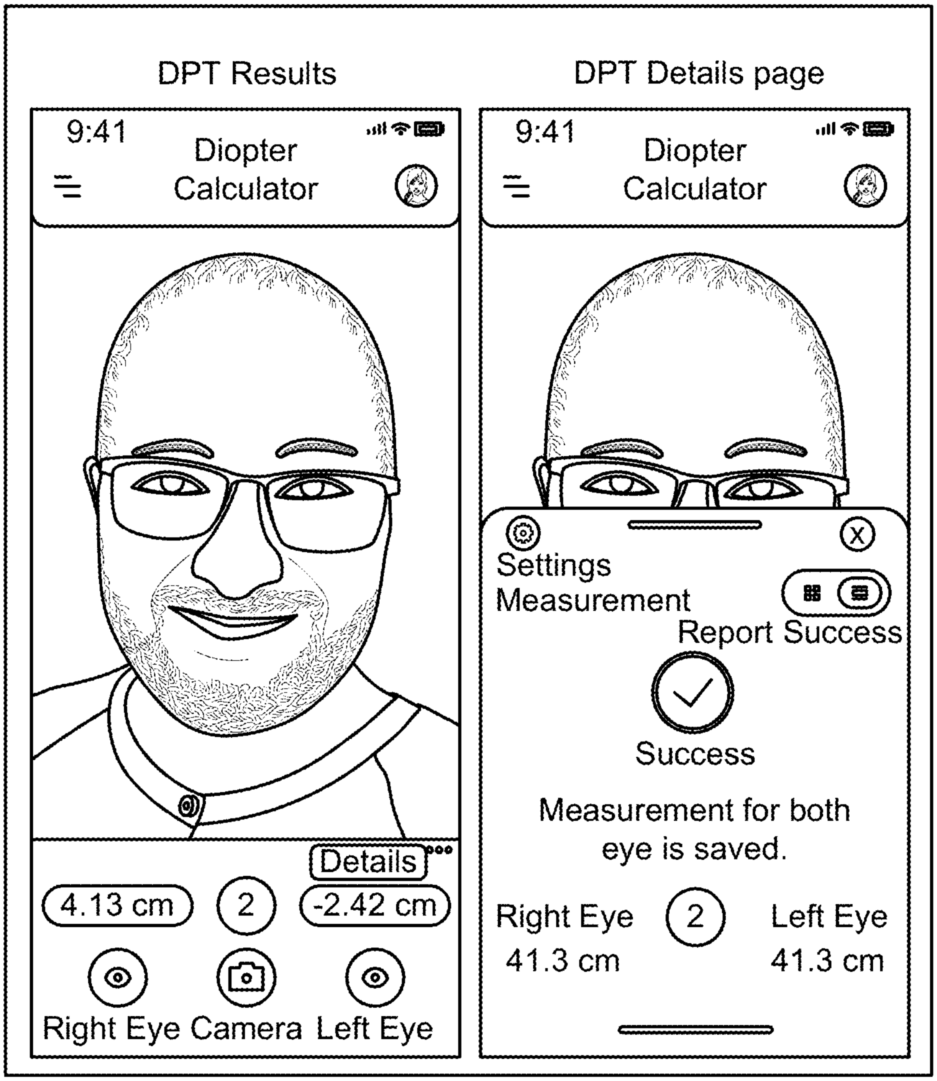

FIGS. 27A-27C depicts an autonomous chatbot widget that helps connect patients to doctors as well as manages simple and complex tasks such as but not limited to, user frequently asked questions, help locating a nearby doctor, and scheduling an appointment. Scheduling an appointment can also be done by utilizing the 'find my doctor' feature and chatting with the doctor depicted in FIGS. 28A-28B. FIGS. 29A and 29B show example evaluation upon sign up feature.

Method 2400 can start at operational block 2410 where the apparatus 2300, for example, can receive an input for a surgical procedure. In some aspects, the surgical procedure may include a cataract surgery, a cataract LASIK, a FemtoSecond surgery, an MIGS implant surgery, a Keratoconus surgery, or the like.

Method 2400 can proceed to operational block 2420 where the apparatus 2300, for example, can determine feedback for the surgical procedure. The feedback can comprise for example instructions for a patient of the surgical procedure, instructions for a physician of the surgical procedure, instructing a patient to practice looking at fixation points to expose four quadrants of a sclera, and other items.

Method 2400 can proceed to operational block 2430 where the apparatus 2300, for example, can receive a user input in response to the feedback.

Method 2400 can proceed to operational block 2450 where the apparatus 2300, for example, can receive feedback from a laser apparatus (e.g., laser apparatus 1025) for the surgical procedure.

In some implementations, method 2400 can additionally or alternatively involve the apparatus 2300, for example, operating VIRA to perform eye tracking verification, treatment angle verification, a patient screen calibration, lab development, wavefront measurements, eye measurements, retina treatments, simulated eye surgeries, or the like. In some aspects, eye tracking verification may include determining a focal point of the eye 506 using a laser. In some aspects, an eye holder (e.g., the eye holder) may beneficially provide depth control of an eye within the holder. For example, the eye holder may allow modifications to a position of the eye within the folder. In some aspects, the method 2400 may include performing a post-treatment review or post-exercise review, where results of the training exercise may be measured and analyzed.

Performance of the method 2400 and/or a portion thereof can allow for improved real-life and real-time feedback for physicians and/or patients during eye surgeries.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of feedback, such as for example sensory, imaging, data feedback, digital feedback, virtual feedback, visual feedback, auditory feedback, or tactile feedback; and input from the user may be received in any form, including acoustic input, speech input, tactile input, and/or the like. Other possible input devices include touch screens or other touch-sensitive devices such as single or multi-point resistive or capacitive trackpads, voice recognition hardware and software, optical scanners, optical pointers, digital image capture devices, push notifications, and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above.

In the descriptions above and in the claims, phrases such as “at least one of” or “one or more of” may occur followed by a conjunctive list of elements or features. The term “and/or” may also occur in a list of two or more elements or features. Unless otherwise implicitly or explicitly contradicted by the context in which it is used, such phrases are intended to mean any of the listed elements or features individually or any of the recited elements or features in combination with any of the other recited elements or features. For example, the phrases “at least one of A and B;” “one or more of A and B;” and “A and/or B” are each intended to mean “A alone, B alone, or A and B together.” A similar interpretation is also intended for lists including three or more items. For example, the phrases “at least one of A, B, and C;” “one or more of A, B, and C;” and “A, B, and/or C” are each intended to mean “A alone, B alone, C alone, A and B together, A and C together, B and C together, or A and B and C together.” The use of the term “based on,” above and in the claims is intended to mean “based at least in part on,” such that a feature or element that is not recited is also permissible.

The illustrated methods are exemplary only. Although the methods are illustrated as having a specific operational flow, two or more operations may be combined into a single operation, a single operation may be performed in two or more separate operations, one or more of the illustrated operations may not be present in various implementations, and/or additional operations which are not illustrated may be part of the methods. In addition, the logic flows depicted in the accompanying FIGURES and/or described herein do not necessarily require the particular order shown, or sequential order, to achieve desirable results. Other implementations may be within the scope of the following claims.

What is claimed is:

1. A method of coordinating a surgical procedure, comprising:
- receiving, by a processor, an input for an ophthalmic surgical procedure;
- determining, by the processor, first feedback for the surgical procedure, wherein the first feedback relates to instructing a patient to practice looking at fixation points to expose four quadrants of a sclera;
- receiving, by the processor and in response to the first feedback, a user input;
- receiving, by the processor, second feedback from a laser apparatus;
- performing, by the processor, eye tracking verification for a user; and
- displaying, by the processor, a graphical display of a virtual assistant.

2. The method of claim 1, wherein displaying the graphical display comprises displaying the graphical display on a user interface.

3. The method of claim 1, wherein the first feedback comprises instructions for a patient of the surgical procedure.

4. The method of claim 3, wherein the user input comprises an eye position of the patient, a voice input, a touch input, or a keyboard input.

5. The method of claim 1, wherein the first feedback informs the patient of a post-operative regimen.

6. The method of claim 1, wherein the first feedback is received via voice over IP (VOIP).

7. The method of claim 1, wherein the second feedback from the laser apparatus relates to an eye tracking verification by determining a focal point of an eye using the laser apparatus.

8. The method of claim 1, further comprising performing a post-treatment review or post-exercise review, where results of a training exercise may be measured and analyzed.

9. The method of claim 1, wherein the ophthalmic surgical procedure includes a cataract surgery, a cataract LASIK, a FemtoSecond surgery, an MIGS implant surgery, or a Keratoconus surgery.

10. The method of claim 1, further comprising reminding, by the processor, a patient to take a prescribed medication and schedule for postoperative visits.

11. The method of claim 10, wherein the reminder is performed via email, text, or mobile application.

12. A system for coordinating an ophthalmic surgical procedure, comprising:
- at least one data processor;
- a display adapted to render a graphical user interface;
- at least one memory including computer program code, the at least one memory and the computer program code configured to, with the at least one data processor:
  - receive, by the at least one data processor, an input for an ophthalmic surgical procedure;
  - determine, by the at least one data processor, first feedback for the surgical procedure, wherein the first feedback relates to instructing a patient to practice looking at fixation points to expose four quadrants of a sclera;
  - receive, by the at least one data processor and in response to the first feedback, a user input;
  - receive, by the at least one data processor, second feedback from a laser apparatus;
  - perform, by the at least one data processor, eye tracking verification for a user; and
  - display, by the at least one data processor, a graphical display of a virtual assistant.

13. The system of claim 12, wherein the first feedback comprises instructions for a patient of the surgical procedure.

14. The system of claim 12, wherein the user input comprises an eye position of the patient, a voice input, a touch input, or a keyboard input.

15. The system of claim 12, wherein the first feedback informs the patient of a post-operative regimen.

16. The system of claim 12, wherein the second feedback from the laser apparatus relates to an eye tracking verification by determining a focal point of an eye using the laser apparatus.

17. The system of claim 12, wherein the ophthalmic surgical procedure includes a cataract surgery, a cataract LASIK, a FemtoSecond surgery, an MIGS implant surgery, or a Keratoconus surgery.

18. A method of coordinating a surgical procedure, comprising:
- receiving, by a processor, an input for an ophthalmic surgical procedure;
- determining, by the processor, first feedback for the surgical procedure, wherein the first feedback is received via voice over IP (VOIP);
- receiving, by the processor and in response to the first feedback, a user input;
- receiving, by the processor, second feedback from a laser apparatus;
- performing, by the processor, eye tracking verification for a user; and
- displaying, by the processor, a graphical display of a virtual assistant.

* * * * *